US008236845B2

(12) United States Patent
Garcia-Lopez et al.

(10) Patent No.: US 8,236,845 B2
(45) Date of Patent: *Aug. 7, 2012

(54) HETEROCYCLYL-SUBSTITUTED-TETRAHYDRO-NAPHTHALEN-AMINE DERIVATIVES, THEIR PREPARATION AND USE AS MEDICAMENTS

(75) Inventors: Monica Garcia-Lopez, Barcelona (ES); Antonio Torrens-Jover, Terrassa (ES); Helmut H. Buschmann, Sant Just Desvern (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 169 days.

This patent is subject to a terminal disclaimer.

(21) Appl. No.: 12/593,464

(22) PCT Filed: Mar. 28, 2008

(86) PCT No.: PCT/EP2008/002488
§ 371 (c)(1),
(2), (4) Date: Nov. 17, 2009

(87) PCT Pub. No.: WO2008/116663
PCT Pub. Date: Oct. 2, 2008

(65) Prior Publication Data
US 2010/0105684 A1 Apr. 29, 2010

(30) Foreign Application Priority Data

Mar. 28, 2007 (EP) .................................... 07384020

(51) Int. Cl.
*A61K 31/415* (2006.01)
*C07D 231/12* (2006.01)
(52) U.S. Cl. ........ 514/403; 514/406; 514/438; 514/657; 548/240; 548/247; 548/356.1; 548/377.1; 549/83; 549/505
(58) Field of Classification Search .................. 514/403, 514/438; 548/240, 356.1; 549/83, 505
See application file for complete search history.

(56) References Cited

U.S. PATENT DOCUMENTS

| 8,097,641 B2 * | 1/2012 | Garcia-Lopez et al. ...... 514/406 |
| 2004/0127502 A1 | 7/2004 | Blackburn et al. |
| 2010/0035936 A1 * | 2/2010 | Garcia-Lopez et al. ...... 514/345 |

FOREIGN PATENT DOCUMENTS

| EP | 1057814 A1 | 12/2000 |
| WO | 96/34849 A | 11/1996 |

OTHER PUBLICATIONS

Vermeulen, et al., J. Med. Chem., 2003, 46(25), pp. 5365-5374.*
Vermeulen, Erik S. et al; "Characterization of the 5-HT7 Receptor Determination of the Pharmacophore for 5-HT7 Receptor Agonism and CoMFA-Based Modeling of the Agonist Binding Site", Journal of Medicinal Chemistry, vol. 46, No. 25, 2003, p. 5371.
Holmberg, Paer et al; "2-Aminotetralin and 2-AminoChroman Derivatives as Selective Serotonin 5-HT7 Receptor Agonists and Antagonists", Journal of Medicinal Chemistry, vol. 47, No. 16, 2004, pp. 3927-3930.
Homan, Evert J. et al; "C5-Substituted derivatives of 5-OMe-BPAT: synthesis and interactions with dopamine D2 and serotonin 5-HT1A receptors", BioOrganic & Medicinal Chemistry, vol. 7, No. 11, 1999, pp. 2541-2548.
Ghoneim, Ola M. et al; "Novel ligands for the human histamine H1 receptor: Synthesis, pharmacology, and comparative molecular field analysis studies of 2-dimethylamino-5-(6)-phenyl-1,2,3,4-tetra hydronaphthalenes", BioOrganic & Medicinal Chemistry, vol. 14, No. 19, 2006, pp. 6640-6658.
Itoh, Katsumi et al; "Synthesis and .beta.-adrenergic blocking activity of 2-(N-substituted amino)-1,2,3,4-tetrahydronaphthalen-1-o1 derivatives", Database Caplus [Online] Chemical Abstracts Service, Columbus, Ohio, 1984 and Chemical & Pharmaceutical Bulletin, vol. 32, No. 1, 1984.

* cited by examiner

*Primary Examiner* — Susannah Chung
(74) *Attorney, Agent, or Firm* — Heslin Rothenberg Farley & Mesiti P.C.

(57) ABSTRACT

The present invention relates to heterocyclyl-substituted-tetrahydro-naphthalen-amine compounds of general formula (I) and compositions thereof, methods for their preparation, and the use of said compounds for the treatment or prophylaxis of various disorders of humans or animals.

26 Claims, No Drawings

HETEROCYCLYL-SUBSTITUTED-TETRAHYDRO-NAPHTHALEN-AMINE DERIVATIVES, THEIR PREPARATION AND USE AS MEDICAMENTS

CROSS REFERENCE TO RELATED APPLICATIONS

This application is a U.S. National Phase filing under 35 U.S.C. §371 of International Application PCT/EP2008/002488, filed Mar. 28, 2008, and published as WO 2008/116663 on Oct. 2, 2008. PCT/EP2008/002488 claimed benefit of priority from European Patent Application No. EP 07384020.9, filed Mar. 28, 2007. The entire contents of each of the prior applications are incorporated herein by reference.

The present invention relates to heterocyclyl-substituted-tetrahydro-naphthalen-amine compounds of general formula (I), methods for their preparation, medicaments comprising these compounds as well as their use for the preparation of a medicament for the treatment of humans or animals The search for new therapeutic agents has been greatly aided in recent years by better understanding of the structure of proteins and other biomolecules associated with target diseases. One important class of proteins that has been the subject of extensive study is the family of 5-hydroxytryptamine (serotonin, 5-HT) receptors. The 5-$HT_7$ receptor discovered in 1993 belongs to this family and has attracted great interest as a valuable new drug target (Terrón, J. A. *Idrugs*, 1998, vol. 1, no. 3, pages 302-310: *"The $5HT_7$ receptor: A target for novel therapeutic avenues?"*).

5-$HT_7$ receptors have been cloned from rat, mouse, guinea pig and human cDNA and exhibit a high degree of interspecies homology (approx. 95%), but it is unique in that it has a low sequence homology with other 5-HT receptors (less than 40%). Its expression pattern, in particular structures of the central nervous system (CNS) (highest in hypothalamus (in particular suprachiasmatic nuclei) and thalamus) and other peripheral tissues (spleen, kidney, intestinal, heart and coronary artery), implicates the 5-$HT_7$ receptor in a variety of functions and pathologies. This idea is reinforced by the fact that several therapeutic agents, such as tricyclic antidepressants, typical and atypical antipsychotics and some 5-$HT_2$ receptor antagonists, display moderate to high affinity for both recombinant and functional 5-$HT_7$ receptors.

Functionally, the 5-$HT_7$ receptor has been implicated in regulation of circadian rhythms in mammals (Lovenberg, T. W. et al. *Neuron*, 1993, 11:449-458 *"A novel adenylyl cyclase-activating serotonin receptor (5-$HT_7$) implicated in the regulation of circadian rhythms"*). It is known that disruption of circadian rhythms is related to a number of CNS disorders including depression, seasonal affective disorder, sleep disorders, shift worker syndrome and jet lag among others.

Distribution and early pharmacological data also suggest that the 5-$HT_7$ receptor is involved in the vasodilatation of blood vessels. This has been demonstrated in vivo (Terrón, J. A., *Br J Pharmacol*, 1997, 121:563-571 *"Role of 5-$HT_7$ receptors in the long lasting hypotensive response induced by 5-hydroxytryptamine in the rat"*). Thus selective 5-$HT_7$ receptor agonists have a potential as novel hypertensive agents.

The 5-$HT_7$ receptor has also been related with the pathophysiology of migraine through smooth muscle relaxation of cerebral vessels (Schoeffter, P. et al., 1996, *Br J Pharmacol*, 117:993-994; Terrón, J. A., 2002, *Eur. J. Pharmacol.*, 439:1-11 *"Is the 5-$HT_7$ receptor involved in the pathogenesis and prophylactic treatment of migraine?"*). In a similar manner, involvement of 5-$HT_7$ in intestinal and colon tissue smooth muscle relaxation makes this receptor a target for the treatment of irritable bowel syndrome (De Ponti, F. et al., 2001, *Drugs*, 61:317-332 *"Irritable bowel syndrome. New agents targeting serotonin receptor subtypes"*). Recently, it has also been related to urinary incontinence (*British J. of Pharmacology*, September 2003, 140(1) 53-60: *"Evidence for the involvement of central 5HT-7 receptors in the micurition reflex in anaesthetized female rats"*).

In view of the potential therapeutic applications of agonists or antagonists of the 5$HT_7$ receptor, a great effort has been directed to find selective ligands. Despite intense research efforts in this area, very few compounds with selective 5-$HT_7$ antagonist activity have been reported (Wesolowska, A., *Polish J. Pharmacol.*, 2002, 54: 327-341, *"In the search for selective ligands of 5-$HT_5$, 5-$HT_6$ and 5-$HT_7$ serotonin receptors"*), yet even fewer 5-HT7-Agonists.

There is still a need to find compounds that have pharmacological activity towards the receptor 5-$HT_7$, being both effective and selective, and having good "drugability" properties, i.e. good pharmaceutical properties related to administration, distribution, metabolism and excretion.

Thus, it was an object of the present invention to provide novel compounds that are suitable in particular as active substances in medicaments.

Said object was achieved by providing as an active compound a heterocyclyl-substituted-tetrahydro-naphthalen-amine derivative of general formula (I)

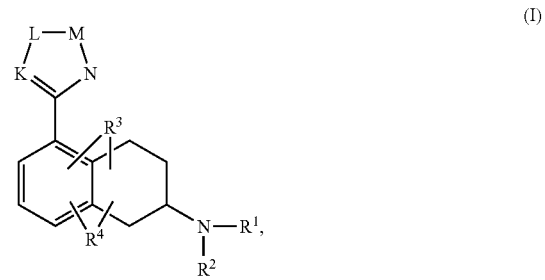

(I)

wherein
K-L-M-J together form
=CH—X—Y=CH—, in which any suitable H may be substituted by $R^6$ and/or $R^7$, and in which X is selected from $NR^8$, O or S, while Y is selected from N or CH;
=CH—X—Y—C(O)—, in which any suitable H may be substituted by $R^6$ and in which one of X and Y is $NR^8$, while the other is selected from $NR^{8a}$, S or O;
=CH—X—Y—C(O)—, in which one of X and Y is $CH_2$, while the other is selected from $NR^8$, S or O, in which any suitable H may be substituted by $R^6$ and/or $R^7$;
=$CR^6$—N=N—C(O)—; or
=$CR^9$—$X_1$=Y—$X_2$=$CR^{9a}$—, in which two of Y, $X_1$ and $X_2$ are CH, while the other is selected from CH or N, in which any suitable H may be substituted by $R^6$;
$R^1$ and $R^2$ are independently from each other a linear or branched, saturated or unsaturated, optionally at least mono-substituted aliphatic radical;
or
$R^1$ and $R^2$ together with their connecting nitrogen are forming an optionally at least mono-substituted heterocyclic ring system;
$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or OH;

$R^9$ and $R^{9a}$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

In a preferred embodiment the following proviso applies:
with the proviso that (2S)-Dimethyl-[5-(1,3,5-trimethyl-1H-pyrazol-4-yl)-1,2,3,4-tetrahydro-naphthalen-2-yl]-amine is excluded.

In another preferred embodiment the following proviso applies:
with the proviso that
(rac)-Dimethyl-[5-(1,3,5-trimethyl-1H-pyrazol-4-yl)-1,2,3,4-tetrahydro-naphthalen-2-yl]-amine; and
(2S)-Dimethyl-[5-(1,3,5-trimethyl-1H-pyrazol-4-yl)-1,2,3,4-tetrahydro-naphthalen-2-yl]-amine;
are excluded.

In another preferred embodiment the following proviso applies:
with the proviso that if K-L-M-J together form =$CR^6$—X—Y=$CR^7$—, in which $R^6$ and $R^7$ are both methyl and in which X is $NR^8$ and Y is N,
$R^1$ and $R^2$ may not both be $CH_3$.

In another preferred embodiment the following proviso applies:
with the proviso that if K-L-M-J together form =CH—X—Y=CH—, in which any suitable H may be substituted by $R^6$ and/or $R^7$ and in which X is $NR^8$ and Y is N, $R^1$ and $R^2$ may not both be $CH_3$.

In another preferred embodiment the following proviso applies:
with the proviso that $R^1$ and $R^2$ may not both be $CH_3$.

In another preferred embodiment the following proviso applies:
with the proviso that 1,2,3,4-tetrahydro-N,N-dimethyl-5-(2,4,5-trimethyl-1H-pyrrol-3-yl)naphthalen-2-amine
is excluded.

The compound according to formula I may be present in the form of a racemic mixture as expressed by formula (I) or maybe present as one of the enantiomers. Thus Formula I may also be expressed as one of its enantiomers [(S) or (R)] thus as Formula I-S or Formula I-R.

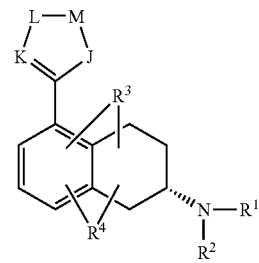

Formula I-S or
Formula (S)-(I)

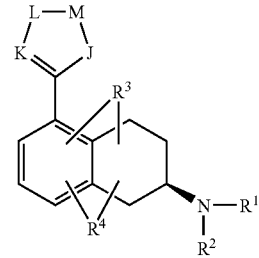

Formula I-R
Formula (R)-(I)

In a very preferred embodiment the compound or compounds according to the invention according to formula (I) is/are 5-$HT_7$ receptor agonists.

A "mono- or polycyclic ring-system" according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-system are preferably 5- or 6-membered.

An "aryl radical" or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

"Alkyl-aryl" or "alkyl-aryl radical" or group is understood as meaning a ring system with at least one aromatic ring but without heteroatoms even in only one of the rings connected to the core through an alkylene $(CH_2)_{1-4}$ group. In this, substitution is referring to a substitution in the ring system, not in the alkylene. An example is benzyl, which can be unsubstituted or monosubstituted or polysubstituted.

In the context of this invention "cycloalkyl radical" or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents $C_3$- or $C_4$-cycloalkyl, $C_{3-5}$-cycloalkyl represents $C_3$-, $C_4$- or $C_5$-cycloalkyl, $C_{3-6}$-cycloalkyl represents $C_3$-, $C_4$-, $C_5$- or $C_6$-cycloalkyl, $C_{3-7}$-cycloalkyl represents $C_3$-, $C_4$-, $C_5$-, $C_6$- or $C_7$-cycloalkyl, $C_{3-8}$-cycloalkyl represents $C_3$-, $C_4$-, $C_5$-, $C_6$-, $C_7$- or $C_8$-cycloalkyl, $C_{4-5}$-cycloalkyl represents $C_4$- or $C_5$-cycloalkyl, $C_{4-6}$-cycloalkyl represents $C_4$-, $C_5$- or $C_6$-cycloalkyl, $C_{4-7}$-cycloalkyl represents $C_4$-, $C_5$-, $C_6$- or $C_7$-cycloalkyl, $C_{4-8}$-cycloalkyl represents $C_4$-, $C_5$-, $C_6$- $C_7$- or $C_8$-cycloalkyl $C_{5-6}$-cycloalkyl represents $C_5$- or $C_6$-cycloalkyl and $C_{5-7}$-cycloalkyl represents $C_5$-, $C_6$- or $C_7$-cycloalkyl. However, mono- or polyunsaturated, preferably monounsaturated, cycloalkyls also in particular fall under the term cycloalkyl as long as the cycloalkyl is not an aromatic system. The cycloalkyl radicals are preferably cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

A "heterocyclyl", a "heterocyclyl radical" or group or "heterocyclic ring system" is understood as meaning heterocyclic ring systems which contain one or more heteroatoms from the group consisting of nitrogen, oxygen and/or sulfur in the ring or ring system, and can also be mono- or polysubstituted. The ring system may consist either of only one saturated or unsaturated or even aromatic ring or may consist of 2, 3 or 4 saturated or unsaturated or even aromatic rings, which are condensed in that between two or more of the rings ring members are shared. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, imidazo-thiazole, benzothiazole, indole, benzotriazole, benzodioxolane, benzodioxane, carbazole and quinazoline.

In connection with mono- or polycyclic ring-system, alkylaryl, aryl radical, cycloalkyl radical, or heterocyclyl radical, "substituted" is understood—unless defined otherwise—as meaning replacement of at least one hydrogen radical on the ring-system of the mono- or polycyclic ring-system, the alkyl-aryl, the aryl radical, the cycloalkyl radical, or the heterocyclyl radical by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; by a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl; a saturated or unsaturated, linear or branched, substituted or unsubstituted —C(O)—O—$C_{1-6}$-alkyl; a substituted or unsubstituted phenyl. Within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents. Therefore, "optionally at least monsubstituted" means either "not substituted" if the option is not fulfilled, "monosubstituted" or "polysubstituted".

In connection with aryl radical, cycloalkyl radical, or heterocyclyl radical, "condensed with" is understood as meaning that the ring-system of the aryl radical, the cycloalkyl radical, or the heterocyclyl radical is sharing two atoms (one) of its ring(s) with a ring of the mono- or polycyclic ring-system it is condensed with.

Aliphatic radicals/groups, as referred to in the present invention, are optionally mono- or polysubstituted and may be branched or linear, saturated or unsaturated. Aliphatic radicals, as defined in the present invention, include alkyl, alkenyl and alkinyl radicals. Unsaturated aliphatic radicals, as defined in the present invention, include alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl.

In the context of this invention, alkyl radical or group is understood as meaning saturated, linear or branched hydrocarbons, which can be unsubstituted or mono- or polysubstituted. Thus unsaturated alkyl is understood to encompass alkenyl and alkinyl groups, like e.g. —CH=CH—$CH_3$ or —C≡C—$CH_3$, while saturated alkyl encompasses e.g. —$CH_3$ and —$CH_2$—$CH_3$. In these radicals, $C_{1-2}$-alkyl represents $C_1$ or $C_2$-alkyl, $C_{1-3}$-alkyl represents $C_1$-, $C_2$- or $C_3$-alkyl, $C_{1-4}$-alkyl represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl, $C_{1-7}$-alkyl represents $C_1$-, $C_2$-, $C_3$-, $C_4$-, $C_5$-, $C_6$- or $C_7$-alkyl, $C_{1-8}$-alkyl represents $C_1$-, $C_2$-, $C_3$-, $C_4$-, $C_5$-, $C_6$-, $C_7$- or $C_8$-alkyl, $C_{1-10}$-alkyl represents $C_1$-, $C_2$-, $C_3$-, $C_4$-, $C_5$-, $C_6$-, $C_7$-, $C_8$-, $C_9$- or $C_{10}$-alkyl and $C_{1-18}$-alkyl represents $C_1$-, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In connection with alkyl, alkylene or aliphatic radical or group—unless defined otherwise—the term "substituted" in the context of this invention is understood as meaning replacement of at least one hydrogen radical by F, Cl, Br, I, $NH_2$, SH or OH; within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH=CH—$CHCl_2$. Therefore, "optionally at least monsubstituted" means either "not substituted" if the option is not fulfilled, "monosubstituted" or "polysubstituted".

The term "alkylene" is understood as meaning a divalent alkyl group like —$CH_2$— or —$CH_2$—$CH_2$—, with $(CH_2)_{3-6}$ being understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$— or $^{14}C$-enriched carbon or $^{15}N$-enriched nitrogen are within the scope of this invention.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, of its salts, solvates or prodrugs.

Particularly preferred are compounds according to the invention of general formula (Ia)

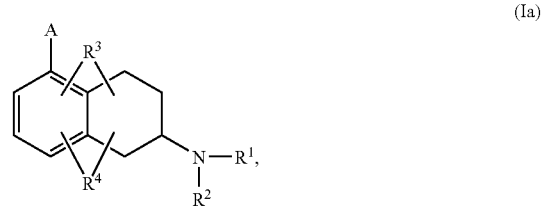

wherein

A is a compound selected from the following group

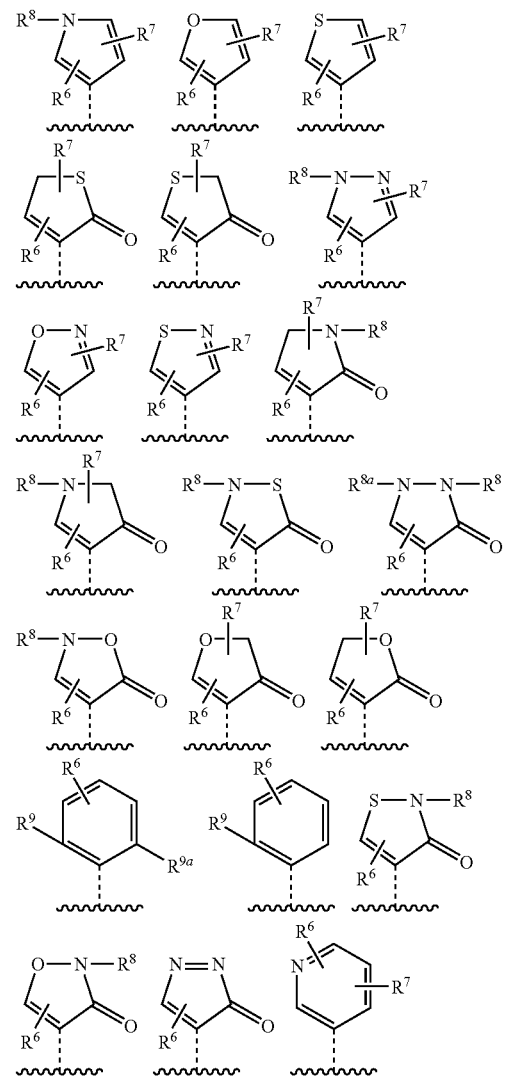

$R^1$ and $R^2$ are independently from each other a linear or branched, saturated or unsaturated, optionally at least mono-substituted aliphatic radical;
or
$R^1$ and $R^2$ together with their connecting nitrogen are forming an optionally at least mono-substituted heterocyclic ring system;
$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;
$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;
$R^8$ and $R^{8a}$ are independently from each other selected from hydrogen; or an aliphatic radical, which is linear or branched, saturated or unsaturated, and optionally at least mono-substituted by F, Cl, Br, I, SH or OH;
$R^9$ and $R^{9a}$ are independently from each other selected from halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

In a preferred embodiment the following proviso applies:
with the proviso that (2S)-Dimethyl-[5-(1,3,5-trimethyl-1H-pyrazol-4-yl)-1,2,3,4-tetrahydro-naphthalen-2-yl]amine is excluded.

In another preferred embodiment the following proviso applies:
with the proviso that
(rac)-Dimethyl-[5-(1,3,5-trimethyl-1H-pyrazol-4-yl)-1,2,3,4-tetrahydro-naphthalen-2-yl]-amine; and
(2S)-Dimethyl-[5-(1,3,5-trimethyl-1H-pyrazol-4-yl)-1,2,3,4-tetrahydro-naphthalen-2-yl]-amine;
are excluded.

In another preferred embodiment the following proviso applies:
with the proviso that if A is a pyrazole, substituted at least in 3 and 5 position by methyl, $R^1$ and $R^2$ may not both be $CH_3$.

In another preferred embodiment the following proviso applies:
with the proviso that if A is pyrazole, $R^1$ and $R^2$ may not both be $CH_3$.

In another preferred embodiment the following proviso applies:
with the proviso that $R^1$ and $R^2$ may not both be $CH_3$.

In another preferred embodiment the following proviso applies:
with the proviso that 1,2,3,4-tetrahydro-N,N-dimethyl-5-(2,4,5-trimethyl-1H-pyrrol-3-yl)naphthalen-2-amine
is excluded.

The compound according to formula (Ia) may be present in the form of a racemic mixture as expressed by formula (Ia) or maybe present as one of the enantiomers. Thus Formula Ia may also be expressed as one of its enantiomers [(S) or (R)] thus as Formula Ia-S or Formula Ia-R.

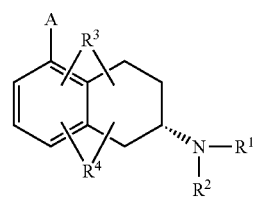

Formula Ia-S

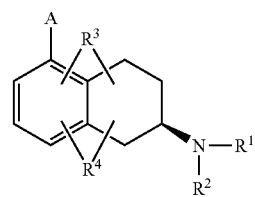

Formula Ia-R

A preferred embodiment of the compounds according to the invention are compounds of general formula (Ia), wherein A is a compound selected from the following group

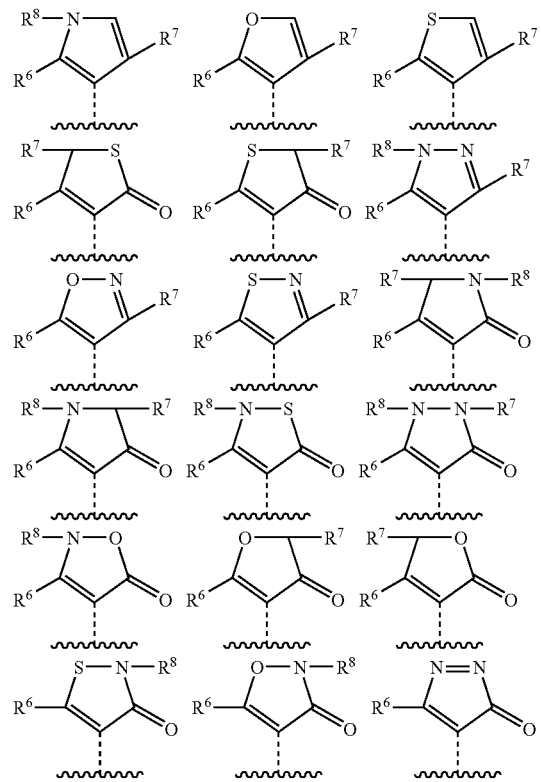

$R^1$ and $R^2$ are independently from each other a linear or branched, saturated or unsaturated, optionally at least mono-substituted aliphatic radical;
or
$R^1$ and $R^2$ together with their connecting nitrogen are forming an optionally at least mono-substituted heterocyclic ring system;
$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or OH.

Another preferred embodiment of the compounds according to the invention are compounds of general formula (Ia), wherein A is a compound selected from the following group

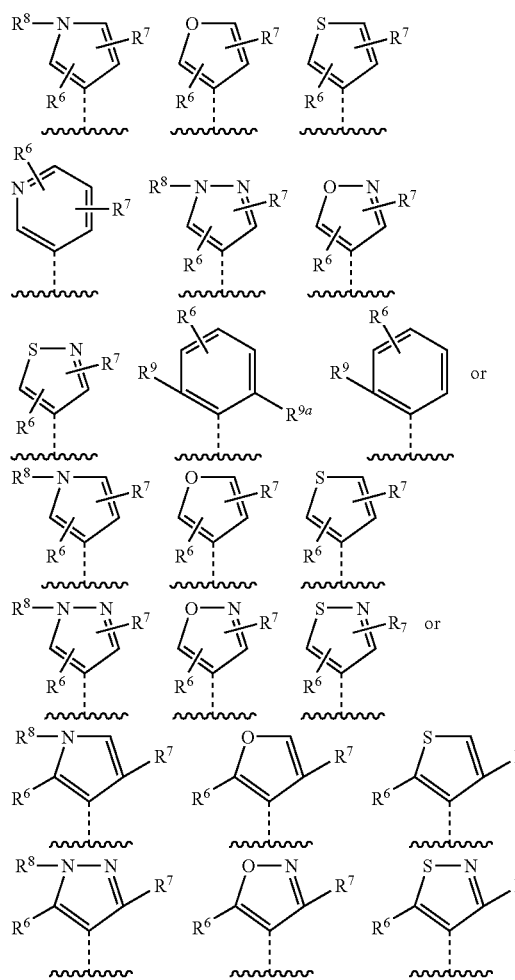

$R^1$ and $R^2$ are independently from each other a linear or branched, saturated or unsaturated, optionally at least mono-substituted aliphatic radical;
or
$R^1$ and $R^2$ together with their connecting nitrogen are forming an optionally at least mono-substituted heterocyclic ring system;
$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ is selected from hydrogen; or an aliphatic radical, which is linear or branched, saturated or unsaturated, and optionally at least mono-substituted by F, Cl, Br, I, SH or OH.

Another preferred embodiment of the compounds according to the invention are compounds of general formula (I) or (Ia), wherein
  $R^1$ and $R^2$ are independently from each other a linear or branched, optionally at least mono-substituted $C_{1-4}$-alkyl radical;
preferably in that
  $R^1$ and $R^2$ are independently from each other a linear or branched $C_{1-4}$-alkyl radical;
more preferably in that
  $R^1$ and $R^2$ are independently from each other $CH_3$, $C_2H_5$ or $C_3H_7$.

Another preferred embodiment of the compounds according to the invention are compounds of general formula (I) or (Ia), wherein
  $R^1$ and $R^2$ together with their connecting nitrogen are forming an optionally at least mono-substituted heterocyclic ring system of 4 to 7 ring members;
preferably in that
  $R^1$ and $R^2$ together with their connecting nitrogen are forming an optionally at least mono-substituted heterocyclic ring system of 5 or 6 ring members;
more preferably in that
  $R^1$ and $R^2$ together with their connecting nitrogen are forming a heterocyclic ring system selected from

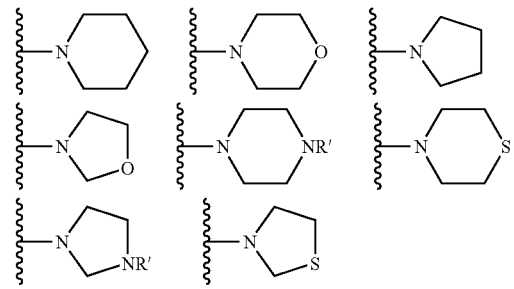

wherein R' is selected from hydrogen or a linear or branched $C_{1-4}$-alkyl radical.

Another preferred embodiment of the compounds according to the invention are compounds of general formula (I) or (Ia), wherein
  $R^3$ and $R^4$ are independently from each other selected from hydrogen; halogen, OH, SH, $NH_2$; a linear or branched, optionally at least mono-substituted $C_{1-4}$-alkyl radical; or O—R with R being a linear or branched, optionally at least mono-substituted $C_{1-4}$-alkyl radical;
preferably in that
  $R^3$ and $R^4$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$, more preferably in that
R³ and R⁴ are H.

Another preferred embodiment of the compounds according to the invention are compounds of general formula (I) or (Ia), wherein
R⁶ and R⁷ are independently from each other selected from hydrogen; halogen, OH, SH, NH₂; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;
preferably in that
R⁶ and R⁷ are independently from each other selected from H, F, Cl, Br, I, OH, SH, NH₂, CH₃, C₂H₅, C₃H₇, C₄H₉, OCH₃, OC₂H₅, OC₃H₇ or OC₄H₉;
more preferably in that
R⁶ and R⁷ are independently from each other selected from H, or CH₃.

Another preferred embodiment of the compounds according to the invention are compounds of general formula (I) or (Ia), wherein
R⁸ is selected from hydrogen; or a $C_{1-4}$-alkyl radical, which is linear or branched, and optionally at least mono-substituted by F, Cl, Br, I, SH or OH;
preferably in that
R⁸ is selected from H, CH₃, C₂H₅, C₃H₇, or C₄H₉;
more preferably in that
R⁸ is selected from H or CH₃.

Another preferred embodiment of the compounds according to the invention are compounds of general formula (I) or (Ia), wherein
R⁹ and R⁹ᵃ are independently from each other selected from hydrogen; F, Cl, Br, I, OH, SH, NH₂; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;
preferably in that
R⁹ and R⁹ᵃ are independently from each other selected from H, F, Cl, Br, OCH₃, OC₂H₅, CF₃, OCF₃, CH₃, C₂H₅, C₃H₇, or C₄H₉;
more preferably in that
R⁸ is selected from F or CH₃.

Another preferred embodiment of the compounds according to the invention are compounds of general formula (I) or (Ia), especially (Ia), wherein
R⁹ and R⁹ᵃ are independently from each other selected from F, Cl, Br, I, OH, SH, NH₂; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;
preferably in that
R⁹ and R⁹ᵃ are independently from each other selected from F, Cl, Br, OCH₃, OC₂H₅, CF₃, OCF₃, CH₃, C₂H₅, C₃H₇, or C₄H₉;
more preferably in that
R⁹ and R⁹ᵃ are independently from each other selected from F or CH₃.

Another preferred embodiment of the compounds according to the invention are compounds of general formula (I) or (Ia), selected from
1-[5-(1,3,5-Trimethyl-1H-pyrazol-4-yl)-1,2,3,4-tetrahydro-naphthalen-2-yl]-piperazine;
1-Methyl-4-[5-(1,3,5-trimethyl-1H-pyrazol-4-yl)-1,2,3,4-tetrahydro-naphthalen-2-yl]-piperazine;
1,3,5-Trimethyl-4-(6-pyrrolidin-1-yl-5,6,7,8-tetrahydro-naphthalen-1-yl)-1H-pyrazole;
1-[5-(1,3,5-Trimethyl-1H-pyrazol-4-yl)-1,2,3,4-tetrahydro-naphthalen-2-yl]-piperidine;
Dipropyl-[5-(1,3,5-trimethyl-1H-pyrazol-4-yl)-1,2,3,4-tetrahydro-naphthalen-2-yl]-amine;
Methyl-propyl-[5-(1,3,5-trimethyl-1H-pyrazol-4-yl)-1,2,3,4-tetrahydro-naphthalen-2-yl]amine;
Diethyl-[5-(1,3,5-trimethyl-1H-pyrazol-4-yl)-1,2,3,4-tetrahydro-naphthalen-2-yl]-amine;
Ethyl-methyl-[5-(1,3,5-trimethyl-1H-pyrazol-4-yl)-1,2,3,4-tetrahydro-naphthalen-2-yl]amine;
Dimethyl-[5-(1-methyl-1H-pyrazol-4-yl)-1,2,3,4-tetrahydro-naphthalen-2-yl]-amine;
[5-(3,5-Dimethyl-isoxazol-4-yl)-1,2,3,4-tetrahydro-naphthalen-2-yl]-dimethyl-amine;
(5-Furan-3-yl-1,2,3,4-tetrahydro-naphthalen-2-yl)-dimethyl-amine;
Dimethyl-(5-thiophen-3-yl-1,2,3,4-tetrahydro-naphthalen-2-yl)-amine;
[5-(2,6-Dimethyl-phenyl)-1,2,3,4-tetrahydro-naphthalen-2-yl]-dimethyl-amine;
[5-(2,6-Difluoro-phenyl)-1,2,3,4-tetrahydro-naphthalen-2-yl]-dimethyl-amine;
Dimethyl-(5-pyridin-3-yl-1,2,3,4-tetrahydro-naphthalen-2-yl)-amine;
optionally in form of one of its stereoisomers, preferably enantiomers or diastereomers, its racemate or in form of a mixture of at least two of its stereoisomers, preferably enantiomers or diastereomers, in any mixing ratio, optionally in form of a salt, preferably a physiologically acceptable salt, more preferably in form of a physiologically acceptable acid addition salt, most preferably a hydrochloride salt, or a corresponding solvate.

Another preferred embodiment of the compounds according to the invention are compounds of general formula (I) or (Ia), selected from
1-[5-(1,3,5-Trimethyl-1H-pyrazol-4-yl)-1,2,3,4-tetrahydro-naphthalen-2-yl]-piperazine;
1-Methyl-4-[5-(1,3,5-trimethyl-1H-pyrazol-4-yl)-1,2,3,4-tetrahydro-naphthalen-2-yl]-piperazine;
1,3,5-Trimethyl-4-(6-pyrrolidin-1-yl-5,6,7,8-tetrahydro-naphthalen-1-yl)-1H-pyrazole;
1-[5-(1,3,5-Trimethyl-1H-pyrazol-4-yl)-1,2,3,4-tetrahydro-naphthalen-2-yl]-piperidine;
Dipropyl-[5-(1,3,5-trimethyl-1H-pyrazol-4-yl)-1,2,3,4-tetrahydro-naphthalen-2-yl]amine;
Methyl-propyl-[5-(1,3,5-trimethyl-1H-pyrazol-4-yl)-1,2,3,4-tetrahydro-naphthalen-2-yl]amine;
Diethyl-[5-(1,3,5-trimethyl-1H-pyrazol-4-yl)-1,2,3,4-tetrahydro-naphthalen-2-yl]-amine;
Ethyl-methyl-[5-(1,3,5-trimethyl-1H-pyrazol-4-yl)-1,2,3,4-tetrahydro-naphthalen-2-yl]amine;
Dimethyl-[5-(1-methyl-1H-pyrazol-4-yl)-1,2,3,4-tetrahydro-naphthalen-2-yl]-amine;
[5-(3,5-Dimethyl-isoxazol-4-yl)-1,2,3,4-tetrahydro-naphthalen-2-yl]-dimethyl-amine;
(5-Furan-3-yl-1,2,3,4-tetrahydro-naphthalen-2-yl)-dimethyl-amine;
Dimethyl-(5-thiophen-3-yl-1,2,3,4-tetrahydro-naphthalen-2-yl)-amine;
[5-(2,6-Dimethyl-phenyl)-1,2,3,4-tetrahydro-naphthalen-2-yl]-dimethyl-amine;
[5-(2,6-Difluoro-phenyl)-1,2,3,4-tetrahydro-naphthalen-2-yl]-dimethyl-amine;

Dimethyl-(5-pyridin-3-yl-1,2,3,4-tetrahydro-naphthalen-2-yl)-amine; or
(2S)-Isopropyl-methyl-[5-(1,3,5-trimethyl-1H-pyrazol-4-yl)-1,2,3,4-tetrahydro-naphthalen-2-yl]-amine;
(2S)-Isopropyl-propyl-[5-(1,3,5-trimethyl-1H-pyrazol-4-yl)-1,2,3,4-tetrahydro-naphthalen-2-yl]-amine;
(2S)-Ethyl-isopropyl-[5-(1,3,5-trimethyl-1H-pyrazol-4-yl)-1,2,3,4-tetrahydro-naphthalen-2-yl]amine;
4-[5-(1,3,5-Trimethyl-1H-pyrazol-4-yl)-1,2,3,4-tetrahydro-naphthalen-2-yl]-morpholine;
[5-(2-Methoxy-phenyl)-1,2,3,4-tetrahydro-naphthalen-2-yl]-dimethyl-amine;
[5-(2,6-Dichloro-phenyl)-1,2,3,4-tetrahydro-naphthalen-2-yl]-dimethyl-amine;
[5-(2-Chloro-6-methoxy-phenyl)-1,2,3,4-tetrahydro-naphthalen-2-yl]-dimethyl-amine;
[5-(2-Methoxy-pyridin-3-yl)-1,2,3,4-tetrahydro-naphthalen-2-yl]-dimethyl-amine;
optionally in form of one of its stereoisomers, preferably enantiomers or diastereomers, its racemate or in form of a mixture of at least two of its stereoisomers, preferably enantiomers or diastereomers, in any mixing ratio, optionally in form of a salt, preferably a physiologically acceptable salt, more preferably in form of a physiologically acceptable acid addition salt, most preferably a hydrochloride salt, or a corresponding solvate.

Another preferred embodiment of the compounds according to the invention are compounds of general formula (I) or (Ia), selected from
[5-(3,5-Dimethyl-1H-pyrazol-4-yl)-1,2,3,4-tetrahydro-naphthalen-2-yl]-dimethyl-amine,
Dimethyl-[5-(1-methyl-1H-pyrazol-4-yl)-1,2,3,4-tetrahydro-naphthalen-2-yl]-amine,
(rac)-Dimethyl-[5-(1,3,5-trimethyl-1H-pyrazol-4-yl)-1,2,3,4-tetrahydro-naphthalen-2-yl]amine; and
(2R)-Dimethyl-[5-(1,3,5-trimethyl-1H-pyrazol-4-yl)-1,2,3,4-tetrahydro-naphthalen-2-yl]-amine;
optionally in form of a salt, preferably a physiologically acceptable salt, more preferably in form of a physiologically acceptable acid addition salt, most preferably a hydrochloride salt, or a corresponding solvate.

Another preferred embodiment of the compounds according to the invention are compounds of general formula (Ia), wherein
A is a compound selected from the following group

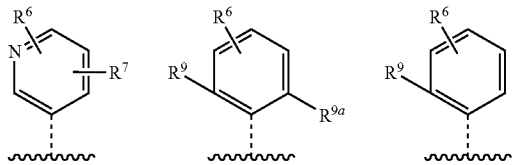

$R^1$ and $R^2$ are $CH_3$;
or
$R^1$ and $R^2$ together with their connecting nitrogen are forming an optionally at least mono-substituted heterocyclic ring system;
$R^3$ and $R^4$ are hydrogen;
$R^6$ is selected from hydrogen; halogen, OH, SH, $NH_2$; an aliphatic radical, which is linear or branched, saturated or unsaturated, and optionally at least mono-substituted by F, Cl, Br, I, SH or OH;
$R^7$ is selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^9$ is selected from halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^{9a}$ is selected from halogen, OH, SH, $NH_2$; an aliphatic radical, which is linear or branched, saturated or unsaturated, and optionally at least mono-substituted by F, Cl, Br, I, SH or OH.

In a preferred embodiment of these compounds according to the invention of general formula (Ia), these compounds are selected from
[5-(2,6-Dimethyl-phenyl)-1,2,3,4-tetrahydro-naphthalen-2-yl]-dimethyl-amine;
[5-(2,6-Difluoro-phenyl)-1,2,3,4-tetrahydro-naphthalen-2-yl]-dimethyl-amine;
Dimethyl-(5-pyridin-3-yl-1,2,3,4-tetrahydro-naphthalen-2-yl)-amine;
[5-(2-Methoxy-phenyl)-1,2,3,4-tetrahydro-naphthalen-2-yl]-dimethyl-amine;
[5-(2,6-Dichloro-phenyl)-1,2,3,4-tetrahydro-naphthalen-2-yl]-dimethyl-amine;
[5-(2-Chloro-6-methoxy-phenyl)-1,2,3,4-tetrahydro-naphthalen-2-yl]-dimethyl-amine;
[5-(2-Methoxy-pyridin-3-yl)-1,2,3,4-tetrahydro-naphthalen-2-yl]-dimethyl-amine;
optionally in form of a salt, preferably a physiologically acceptable salt, more preferably in form of a physiologically acceptable acid addition salt, most preferably a hydrochloride salt, or a corresponding solvate.

In another aspect the present invention also provides a process for the preparation of compounds of general formula (I), according to Scheme 4A, wherein $R^1$, $R^2$, $R^3$, $R^4$, K, L, M and J have the meaning given above.

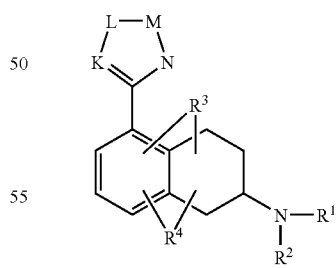

The compounds of general formula (I) can be prepared by catalytic cross-coupling reactions, which include the Kumada-Corriu-Tamao, Negishi, Stille, Hiyama, Suzuki-Miyaura, Heck, Sonogashira and other cross-coupling reactions known to those skilled in the art. More preferably, the compounds of general formula (I) can be prepared by cross-coupling Suzuki reaction of boronic acids or boronate esters of general formula (III) or (IIIa),

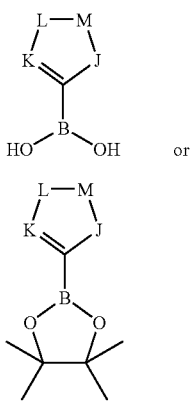

(III)

(IIIa)

wherein K, L, M and J have the meaning given above, is reacted with a compound according to general formula (XII)

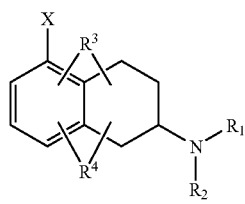

(XII)

wherein $R^1$, $R^2$, $R^3$ and $R^4$ have the meaning given above, and X represents halogen, preferably bromide, OH, OMe or O-triflate group, in a suitable reaction medium, in the presence of a palladium catalyst, a suitable ligand and at least one base. This process can be performed by subjecting the reaction mixture to reflux by conventional heating for a period of time sufficient to achieve the title compound (I), or by microwave radiation, preferably for 1 to 10 minutes, and at a temperature between 100 to 120° C.

Preparation of compounds of general formula (XII) can be achieved by two consecutive reductive amination reactions of aldehydes of general formula (V) and (XIII), $R^1$CHO (V), $R^2$CHO (XIII)

wherein $R^1$ and $R^2$ have the meaning given above, with a compound of general formula (XIV), (XIV)

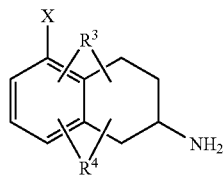

wherein X, $R^3$ and $R^4$ have the meaning described above. The reductive amination is performed by reaction of a mixture comprising a compound of general formula (V) or (XIII), and amino compound of general formula (XIV) and a reducing agent in a suitable reaction medium, for a period of time sufficient to achieve the compound (XII). The reductive amination reaction can also be performed under microwave radiation preferably for 1 to 10 minutes, and at a temperature between 90 to 120° C. The use of microwave irradiation limits the formation of undesirable secondary reaction products, compared to what is obtained in a conventional reductive amination procedure.

This process can be performed as a direct reaction when the carbonyl compound of general formula (V) or (XIII) and the amine compound of general formula (XIV) are mixed with the reducing agent without prior formation of the intermediate imine or iminium salt. A stepwise or indirect reaction involves the reduction of the preformatted imine in a separate step.

The choice of the reducing agent can be conventionally made by those skilled in the art. Reducing agents useful in this procedure include hydrogen and a catalyst, zinc and HCl, sodium cyanoborohydride, lithium cyanoborohydride, tetrabutylammonium cyanoborohydride, cyanoborohydride on a solid support, sodium cyanoborohydride and dehydrating agents, sodium cyanoborohydride and titanium additives, sodium cyanoborohydride and zinc halide additives, sodium borohydride, sodium borohydride and dehydrating agents, sodium borohydride and titanium additives, sodium borohydride and zinc salt additives, lithium borohydride, potassium borohydride, polymer-supported borohydride, borohydride exchange resin with nickel acetate or palladium acetate, sodium triacetoxyborohydride, sodium triacetoxyborohydride and additives, tetramethylammonium triacetoxyborohydride, sodium cyano-9-borabicyclo[3.3.1]nonane, lithium triethylborohydride, lithium tri(sec-butyl)borohydride, sodium diisopinocampheylcyanoborohydride, amine boranes, borane-pyridine complex and alkylamine boranes. Sodium triacetoxyborohydride is particularly preferred because is non-toxic and generally does not reduce the carbonyl group prior to imine formation.

Compound of general formula (XIV) could be obtained from compounds of general formula (XV) by means of a hydrogenation reaction in the presence of a catalyst, especially a palladium catalyst, in a suitable reaction medium, (XV)

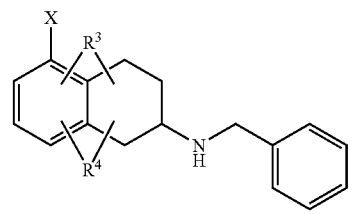

wherein X, $R^3$ and $R^4$ have the meaning described above.

Compounds of general formula (XV) can be prepared by reductive amination reaction of benzylamine with a compound of general formula (XVI), (XVI)

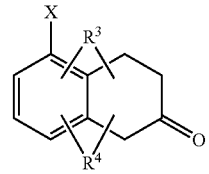

wherein X, $R^3$ and $R^4$ have the meaning given above. The reductive amination reaction can be performed following the methods described above.

The compounds of general formulas (III), (IIIa), (V), (XIII) and (XVI) are either commercially available or can be produced according to methods known to those skilled in the art.

Suitable reaction media are e.g. organic solvents, such as ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents preferably ethyl acetate, triethylamine, pyridine, dimethulsulfoxide, dimethylformamide, hexamethylphosphoramide, acetonitrile, acetone or nitromethane are included. Mixtures based one or more of the above mentioned solvents and water may also be used.

According to the invention, the bases that may be used in the process are generally organic or inorganic bases, preferably alkali metal hydroxides, e.g. sodium hydroxide or potassium hydroxide, or obtained from other metals such as barium hydroxide or different carbonates, preferably potassium carbonate, sodium carbonate, calcium carbonate or alkoxydes, e.g. sodium methoxide potassium methoxide, sodium ethoxide, potassium ethoxide or potassium tert-butoxide, or organic amines, preferably triethylamine, diisopropylethylamine or heterocycles, e.g. 1,4-diazabicyclo[2.2.2]octane, 1,8-diazabicyclo5.4.0]undec-7-ene, pyridine, diamino pydine, dimethylaminopyridine, methylpiperidine or morpholine. Alkali metals such as sodium or its hydrides, e.g. sodium hydride, may also be used.

The preparation of compounds of general formula (I) is illustrated in scheme 4A:

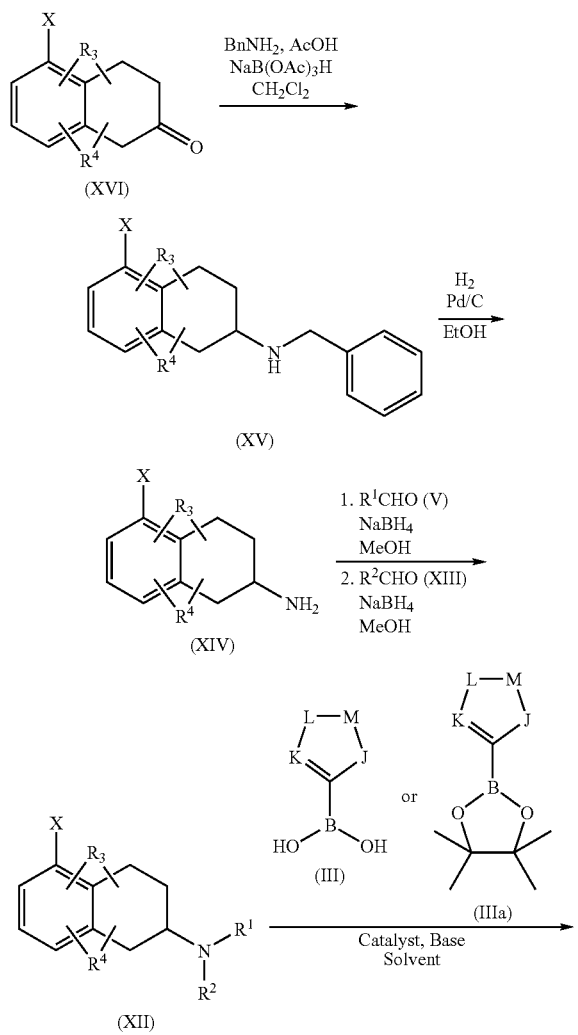

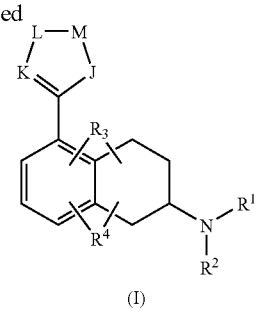

Enantiomerically pure compounds of general formula (S)-(XV) or (R)-(XV),

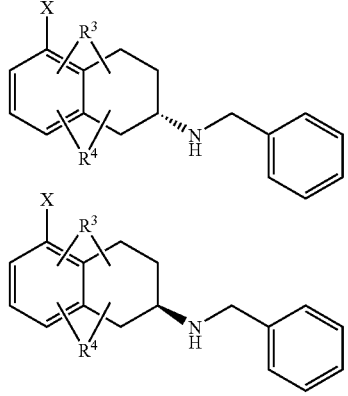

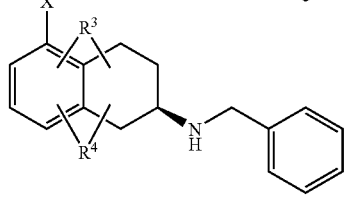

wherein X, $R^3$ and $R^4$ have the meaning described above, are obtained from racemic compounds of general formula (XV) by standard separation procedures known to those skilled in the art, e.g. chromatographic methods or crystallization with chiral reagents, preferably mandelic acid or di-p-toluiltartaric acid, as illustrated in Scheme 4B. Crystallization with (S)-(+)-mandelic acid or L-di-p-toluiltartaric acid leads to (S) enantiomer forms of compounds depicted in Scheme 4B, whereas crystallization with (R)-(−)-mandelic acid leads to (R) enantiomer forms of these compounds.

Subsequent preparation of enantiomerically pure compounds of general formula (S)-(I) or (R)-(I) by this method, may proceed as described above and is illustrated for compounds of general formula (S)-(I) in Scheme 4B:

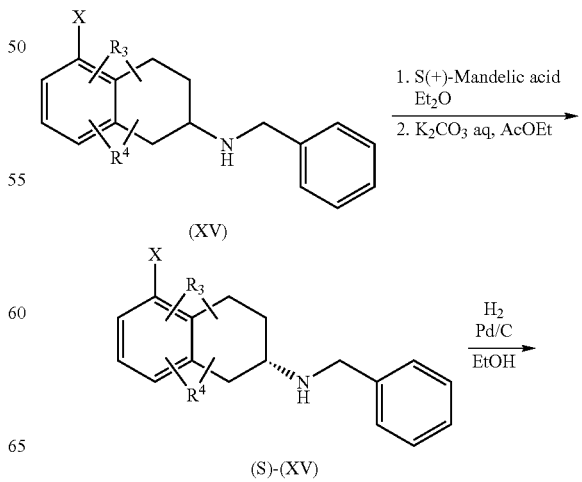

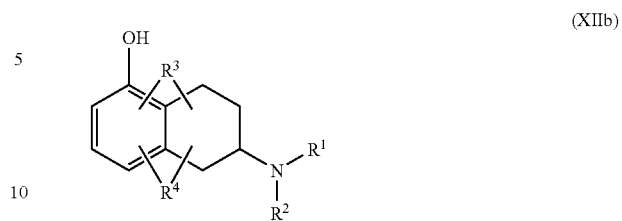

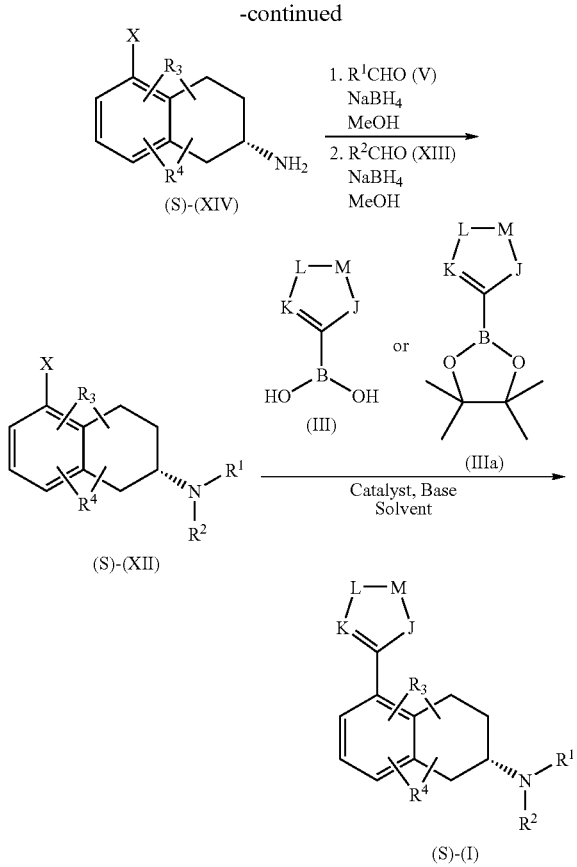

ence of a base and in a suitable reaction medium, with compounds of general formula (XIIb),

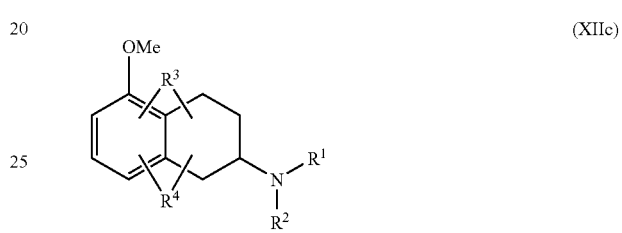

wherein $R^1$, $R^2$, $R^3$ and $R^4$ have the meaning described above.

Hydroxyl compounds of general formula (XIIb) are obtained from the methoxy compounds of general formula (XIIc) by heating in HBr 48% at 125° C., wherein $R^1$, $R^2$, $R^3$ and $R^4$ have the meaning described above. Demethylation of compounds of general formula (XIIc) to obtain compounds of general formula (XIIb) can also be achieved by reaction with $BBr_3$ in a suitable reaction medium, or by other methods known to those skilled in the art.

Compounds of general formula (XIIc) could be prepared by two consecutive reductive amination reactions from amino compounds of general formula (XIV) or (XIVa) as described above (Scheme 4A). In an alternative synthetic process, compounds of general formula (XVI) or (XVIa) can directly afford compounds of general formula (XIIc) through a reductive amination with secondary amines of general formula (XIX), $$HNR^1R^2 \qquad (XIX)$$

wherein $R^1$, and $R^2$ have the meaning given above, in the conditions described above.

The bases that may be used in the process and the suitable reaction media are those described above.

This alternative method for the preparation of compounds of general formula (Ia) is illustrated in scheme 5A:

In another aspect, the present invention also provides a process for the preparation of compounds of general formula (I), in the particular case in which X is OH, OMe or O-triflate group, according to Scheme 5A.

Preparation of compounds of general formula (XIIa), wherein $R^1$, $R^2$, $R^3$ and $R^4$ have the meaning described above, can be achieved by reaction of triflic anhydride, in the pres- Scheme 5A

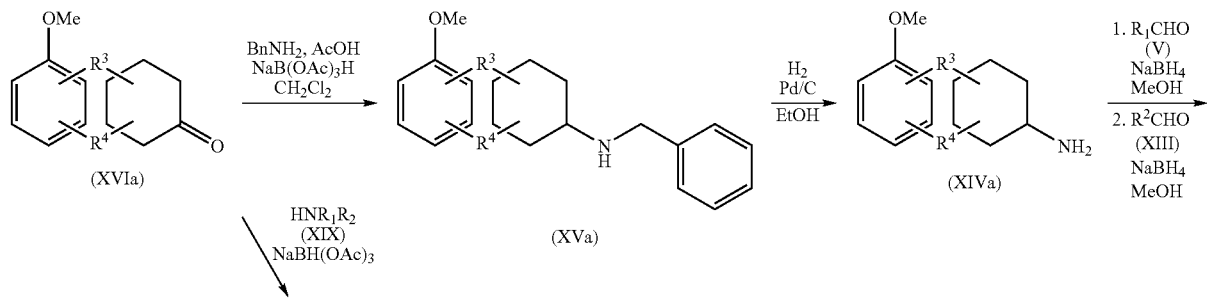

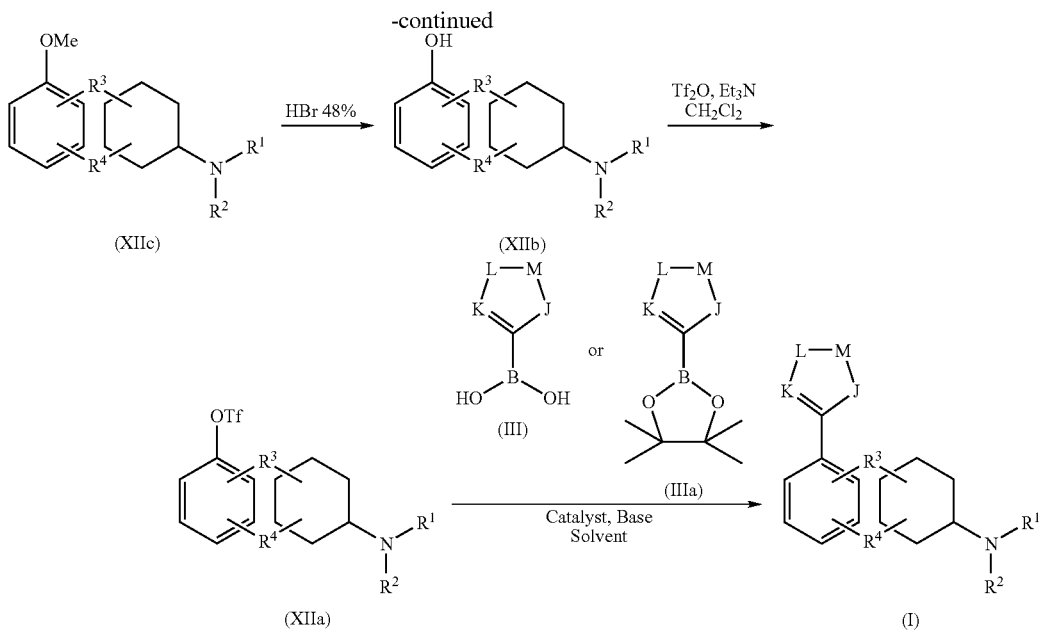

Enantiomerically pure compounds of general formula (S)-(XVa),

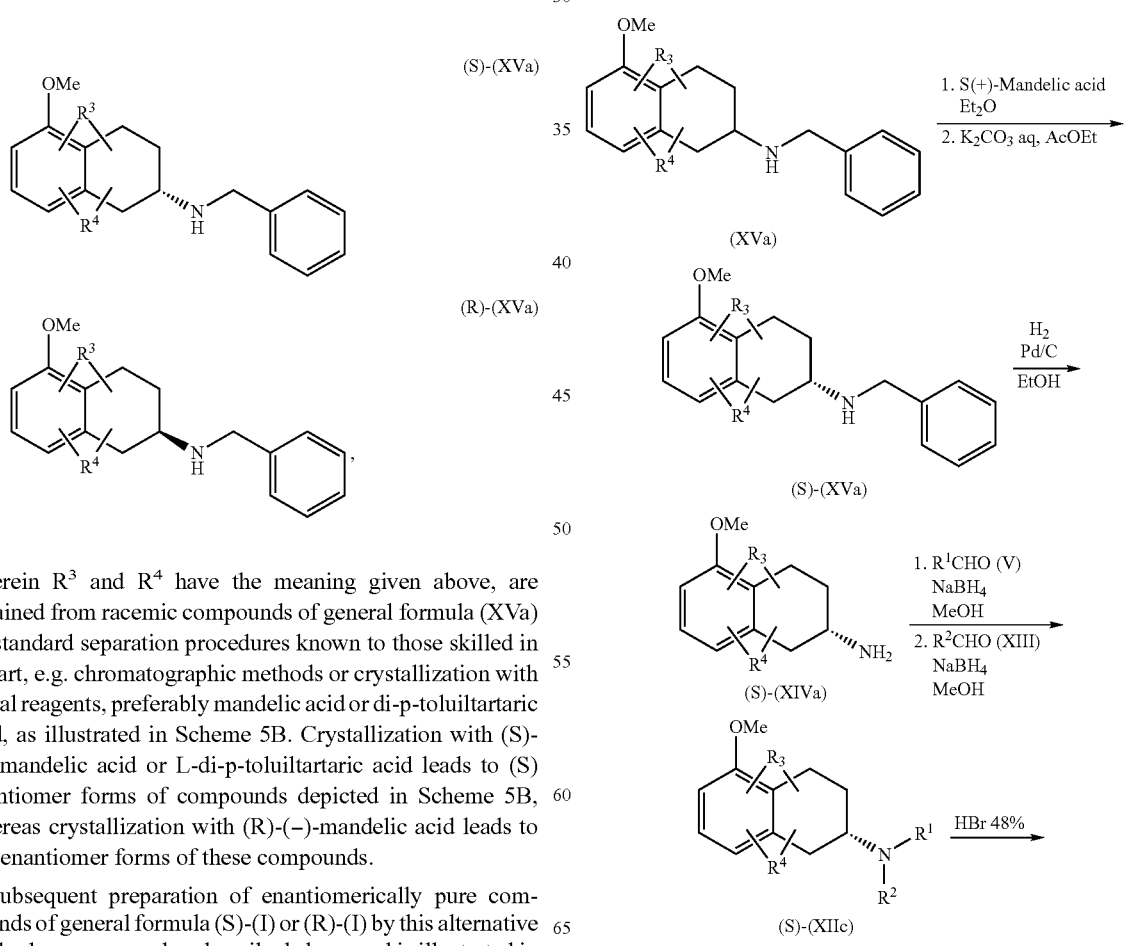

wherein $R^3$ and $R^4$ have the meaning given above, are obtained from racemic compounds of general formula (XVa) by standard separation procedures known to those skilled in the art, e.g. chromatographic methods or crystallization with chiral reagents, preferably mandelic acid or di-p-toluiltartaric acid, as illustrated in Scheme 5B. Crystallization with (S)-(+)-mandelic acid or L-di-p-toluiltartaric acid leads to (S) enantiomer forms of compounds depicted in Scheme 5B, whereas crystallization with (R)-(−)-mandelic acid leads to (R) enantiomer forms of these compounds.

Subsequent preparation of enantiomerically pure compounds of general formula (S)-(I) or (R)-(I) by this alternative method, may proceed as described above and is illustrated in Scheme 5B for compounds of general formula (S)-(1):

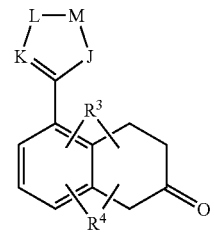

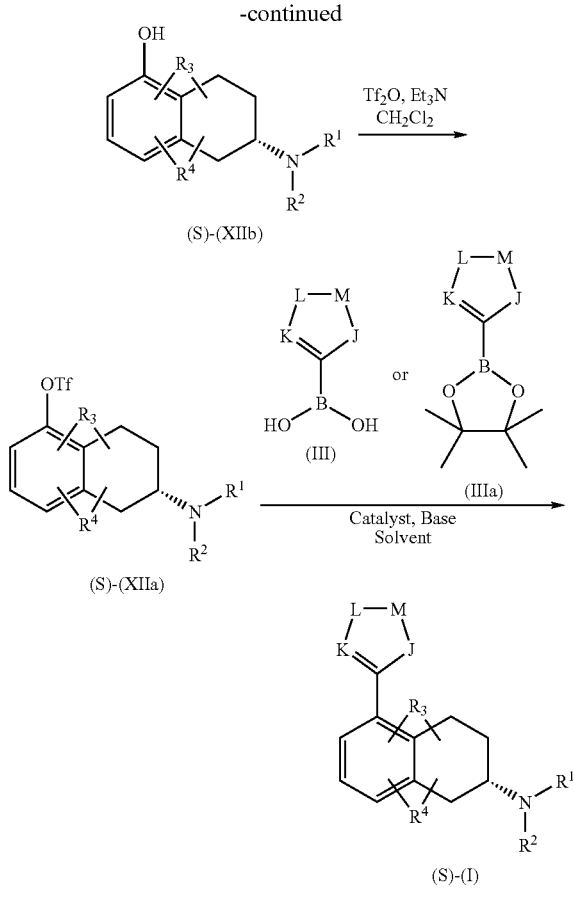

In a further aspect, the present invention also provides an alternative process for the preparation of compounds of general formula (I), according to Scheme 6. According to this process, at least one compound of general formula (XVII),

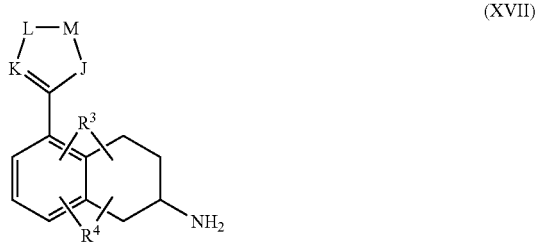

(XVII)

wherein $R^3$, $R^4$, K, L, M and J have the meaning given above, is subjected to two consecutive reductive amination reaction with aldehydes of general formula (V) and (XIII), $R^1CHO$ (V), $R^2CHO$ (XIII)

wherein $R^1$ and $R^2$ have the meaning given above. The reductive amination reaction could be performed following the methods described above.

Amino compounds of general formula (XVII) are obtained by reductive amination with ammonia of carbonyl compounds of general formula (XVIII), in the conditions described above,

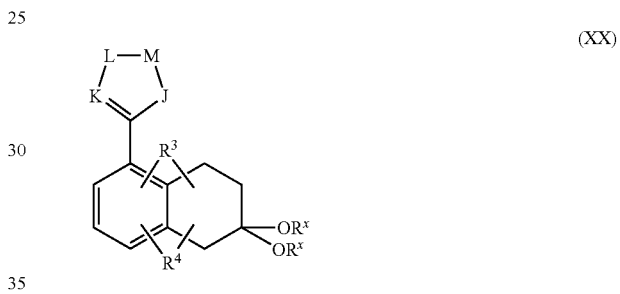

wherein $R^3$, $R^4$, K, L, M and J have the meaning given above. Compounds of general formula (XVIII) can directly afford compounds of general formula (I) through a reductive amination with secondary amines of general formula (XIX), $HNR^1R^2$ (XIX)

wherein $R^1$, and $R^2$ have the meaning given above, in the conditions described above.

Preparation of compounds of general formula (XVIII) can be achieved by hydrolysis of compounds of general formula (XX),

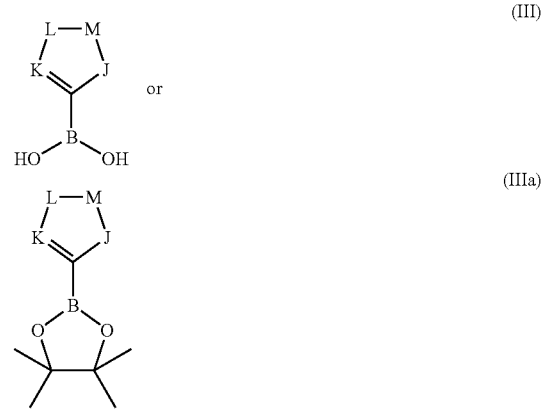

with $R^x$ being hydrogen or an aliphatic radical, which is linear or branched, saturated or unsaturated, and optionally at least mono-substituted by F, Cl, Br, I, SH or OH. Both $R^x$ together with the bridging oxygen atoms can also form a saturated or unsaturated, optionally at least mono-substituted 5- or 6-membered-heterocyclic ring, which may be condensed with an optionally at least mono-substituted mono- or polycyclic ring system. $R^3$, $R^4$, K, L, M and J have the meaning given above.

The compounds of general formula (XX) can be prepared by cross-coupling Suzuki reaction of boronic acids or boronate esters of general formula (III) or (IIIa), wherein K, L, M and J have the meaning described above, with at least one compound of general formula (XXI),

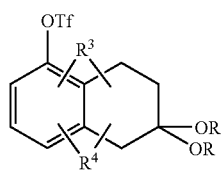
(XXI)

wherein R, R³ and R⁴ have the meaning described above. Suzuki reaction could be performed following the methods described above.

Compounds of general formula (XXI) are obtained by reaction of triflic anhydride, in the presence of a base and in a suitable reaction medium, of compounds of general formula (XXII),

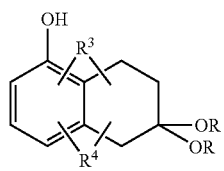
(XXII)

wherein R, R³ and R⁴ have the meaning described above.

Ketal compounds of general formula (XXII) could be formed by treatment of carbonyl compounds of general formula (XXIII),

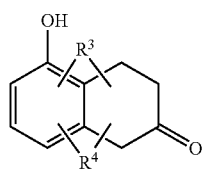
(XXIII)

wherein R³ and R⁴ have the meaning described above, with an alcohol (R—OH) in the presence of acid catalysts.

Hydroxyl compounds of general formula (XXIII) are obtained from the methoxy compounds of general formula (XVIa) by heating in HBr 48% at 125° C.,

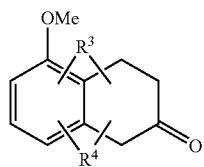
(XVIa)

wherein R³ and R⁴ have the meaning described above. Demethylation of compounds of general formula (XVIa) to obtain compounds of general formula (XXIII) can also be achieved by reaction with BBr₃ in a suitable reaction medium, or by other methods known to those skilled in the art.

The bases that may be used in the process and the suitable reaction media are those described above.

This alternative method for the preparation of compounds of general formula (I) is illustrated in scheme 6:

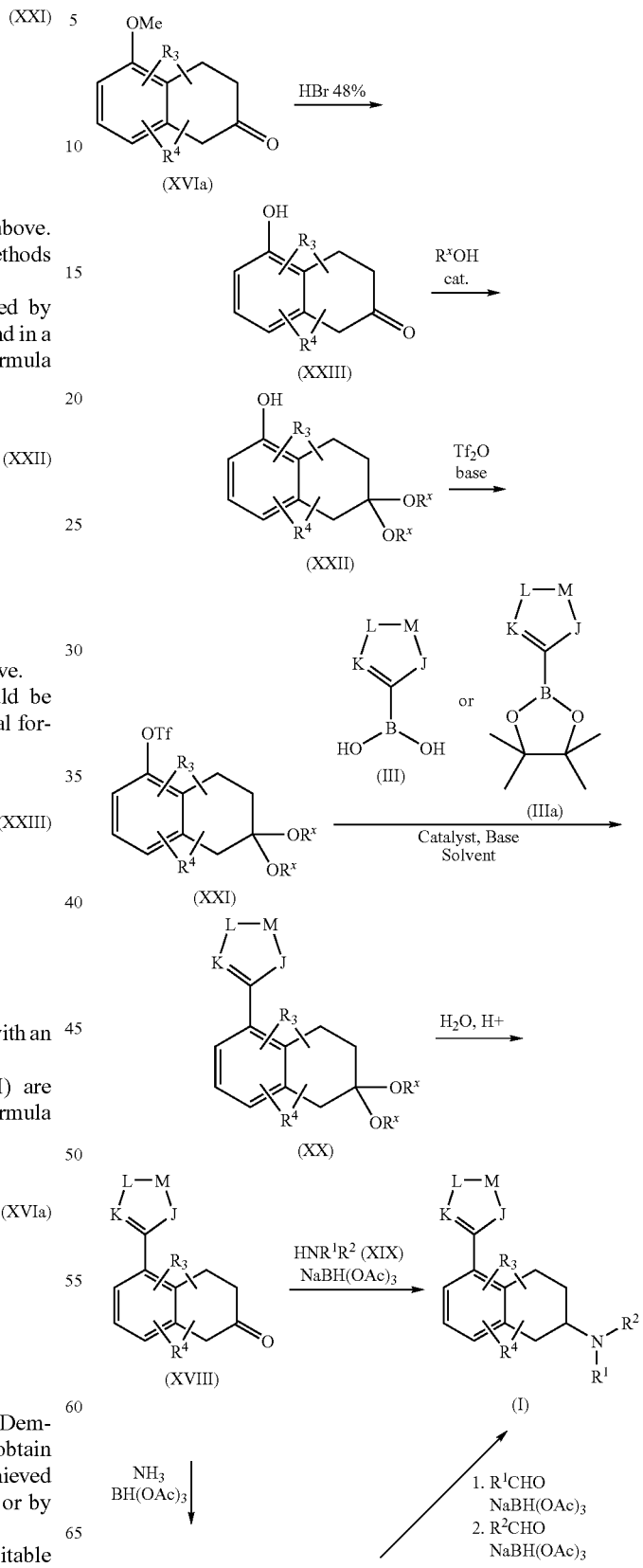

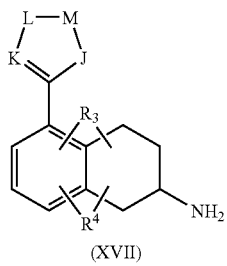

(XVII)

In a further aspect, the present invention also provides an alternative process for the preparation of compounds of general formula (I), according to scheme 7. According to this process, at least one compound of general formula (XXIV),

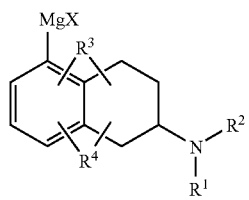

(XXIV)

wherein $R^1$, $R^2$, $R^3$ and $R^4$ have the meaning given above and X represents halogen, preferably bromide, is subjected to Kumada-Corriu cross-coupling reaction with at least one compound of general formula (XXV),

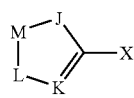

(XXV)

wherein K, L, M and J have the meaning given above and X represents halogen, preferably bromide, in a suitable reaction medium, in the presence of a palladium catalyst, a suitable ligand and at least one base.

Preparation of compounds of general formula (XXIV) can be achieved by Grignard reaction of compounds of general formula (XII),

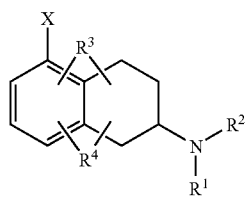

(XII)

wherein $R^1$, $R^2$, $R^3$ and $R^4$ have the meaning given above and X represents halogen, preferably bromide.

The compounds of general formula (XXV) are either commercially available or can be produced according to methods known to those skilled in the art.

The synthesis of compounds of general formula (XII) can be performed according to the methods described above (Scheme 4A).

Suitable reaction media are those described above.

The bases that may be used in the process are those described above.

This alternative method for the preparation of compounds of general formula (I) is illustrated in scheme 7:

Scheme 7

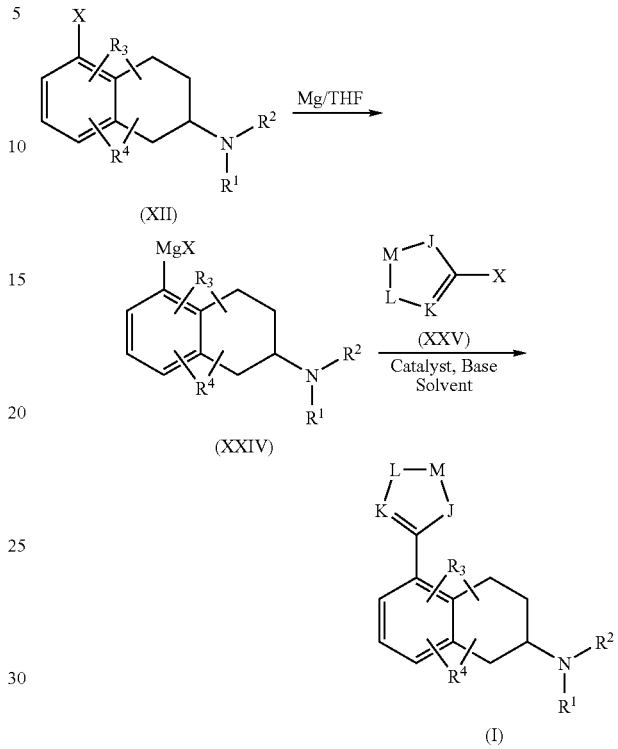

Preparation of enantiomerically pure compounds of general formula (S)-(I) can also be achieved by this alternative method when using compounds of general formula (S)-(XII) as starting material. Compounds of general formula (S)-(XII) can be obtained as described above (scheme 4B).

In another aspect, the present invention also provides an alternative process for the preparation of compounds of general formula (I), according to Scheme 8, wherein $R^1$, $R^2$, $R^3$, and $R^4$, have the meaning given above and K-L-M-J together form:

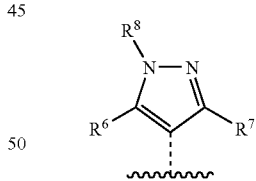

wherein $R^6$, $R^7$ and $R^8$ have the meaning described above.

The compounds of general formula (XXVI), (XXVI)

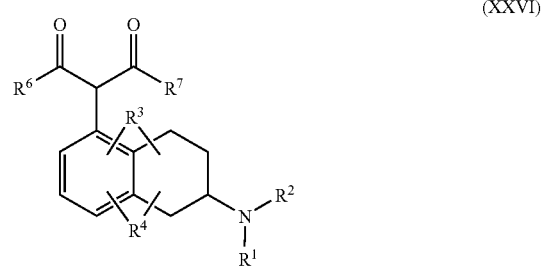

wherein $R^1$, $R^2$, $R^3$, $R^4$, $R^6$ and $R^7$ have the meaning described above are reacted with compounds of general formula (XXVII),

(XXVII)

wherein $R^8$ has the meaning described above, in a suitable reaction media to give the title compounds of general formula (I).

Preparation of compounds of general formula (XXVI) can be achieved by Cu catalyzed nucleophilic substitution reaction of compounds of general formula (XXVIII),

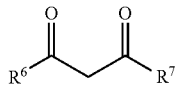
(XXVIII)

wherein $R^6$ and $R^7$ have the meaning described above, with compounds of general formula (XII),

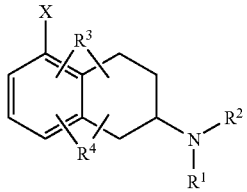
(XII)

wherein $R^1$, $R^2$, $R^3$ and $R^4$ have the meaning given above and X represents halogen, preferably iodide or bromide in a suitable reaction medium, in the presence of CuX, and at least one base.

The compounds of general formulas (XXVII) and (XXVIII) are either commercially available or can be produced according to methods known to those skilled in the art.

Suitable reaction media are those described above.

The bases that may be used in the process are those described above.

Starting compounds of general formula (XII) can be prepared according to Scheme 4A.

This alternative method for the preparation of compounds of general formula (I) is illustrated in scheme 8:

Scheme 8

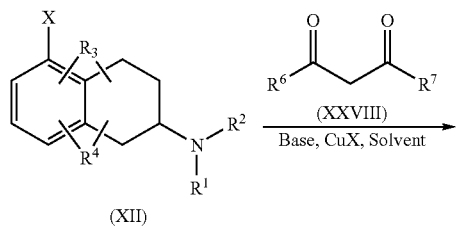

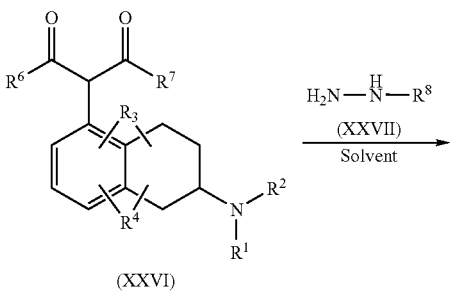
(XXVI)

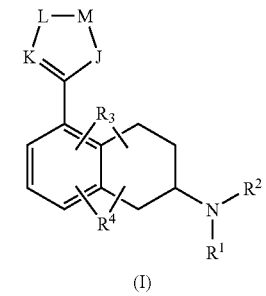
(I)

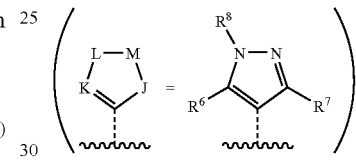

Preparation of enantiomerically pure compounds of general formula (S)-(I) can also be achieved by this alternative method when using compounds of general formula (S)-(XII) as starting material. Compounds of general formula (S)-(XII) can be obtained as described above (scheme 4B).

In a further aspect the present invention also provides processes for the enantioselective synthesis of compounds of general formula (S)-(I) and (R)-(I). Some of these methods are depicted in Schemes 9, 10, 11, 12 and 13.

According to the process illustrated in Scheme 9, preparation of compounds of general formula (S)-(I) can be achieved by reaction of at least one compound of general formula (III) or (IIIa),

(III)

or

(IIIa)

wherein K, L, M and J have the meaning given above, by means of cross-coupling Suzuki reaction with at least one compound of general formula (S)-(XIIa),

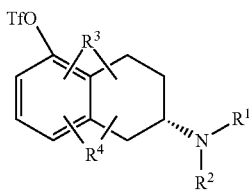

(S)-(XIIa)

wherein $R^1$, $R^2$, $R^3$ and $R^4$, have the meaning given above, in a suitable reaction medium, in the presence of a palladium catalyst, a suitable ligand and at least one base.

Preparation of compounds of general formula (S)-(XIIa) can be achieved by reaction of triflic anhydride, in the presence of a base and in a suitable reaction medium, with compounds of general formula (S)-(XIIb),

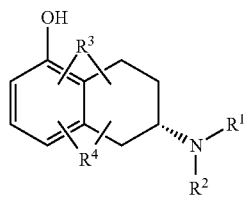

(S)-(XIIb)

wherein $R^1$, $R^2$, $R^3$ and $R^4$ have the meaning described above.

Hydroxyl compounds of general formula (S)-(XIIb) are obtained from the methoxy compounds of general formula (S)-(XIIc) by heating in HBr 48% at 125° C.,

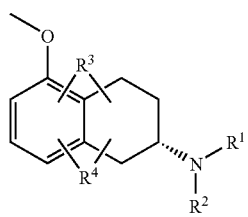

(S)-(XIIc)

wherein $R^1$, $R^2$, $R^3$ and $R^4$ have the meaning described above. Demethylation of compounds of general formula (S)-(XIIc) to obtain compounds of general formula (S)-(XIIb) can also be achieved by reaction with $BBr_3$ in a suitable reaction medium, or by other methods known to those skilled in the art.

Preparation of compounds of general formula (S)-(XIIc) can be achieved by two consecutive reductive amination reactions of aldehydes of general formula (V) and (XIII), $R^1CHO$ (V), $R^2CHO$ (XIII)

wherein $R^1$ and $R^2$ have the meaning given above, with a compound of general formula (S)-(XIVa),

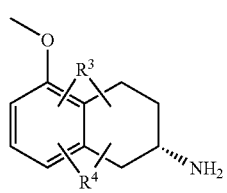

(S)-(XIVa)

wherein $R^3$ and $R^4$ have the meaning described above. The reductive amination reaction could be performed following the methods described above.

Compounds of general formula (S)-(XIVa) are obtained by palladium catalyzed hydrogenation of azide compounds of general formula (XXIX),

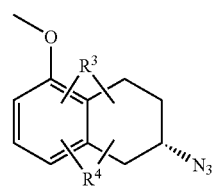

(XXIX)

wherein $R^3$ and $R^4$ have the meaning given above.

Compounds of general formula (XXIX) can be prepared by treatment with sodium azide in a suitable reaction medium of compounds of general formula (XXX),

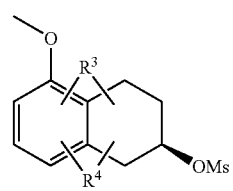

(XXX)

wherein $R^3$ and $R^4$ have the meaning given above.

In an alternative synthetic process, compounds of general formula (XXX) can directly afford some compounds of general formula (S)-(XIIc) through a reaction with secondary amines of general formula (XIX), $HNR^1R^2$ (XIX)

wherein $R^1$ and $R^2$ have the meaning given above.

Hydroxyl compounds of general formula (XXXI),

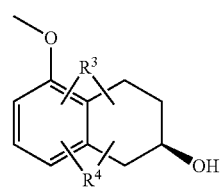

(XXXI)

wherein $R^3$ and $R^4$ have the meaning described above are converted into the corresponding methanesulfonate compounds of general formula (XXX) by treatment with methanesulfonyl chloride in a suitable reaction medium and in the presence of at least one base.

Compounds of general formula (XXXI) are obtained by regioselective epoxide ring opening of compounds of general formula (XXXII),

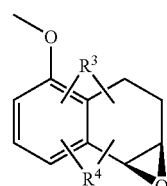

(XXXII)

wherein $R^3$ and $R^4$ have the meaning described above, in the presence of a reducing agent and in a suitable reaction medium.

Chiral epoxides of general formula (XXXII) are prepared from dihydronaphthalene compounds of general formula (XXXIII),

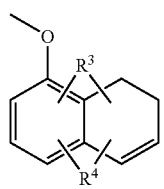

(XXXIII)

wherein $R^3$ and $R^4$ have the meaning described above, in the conditions for the Jacobsen epoxidation known to those skilled in the art.

Compounds of general formula (R)-(I) can also be obtained following this process by using the suitable chiral Jacobsen catalyst to prepare the enantiomer of compounds of general formula (XXXII).

The compounds of general formulas (III), (IIIa), (V), (XIII) and (XXXIII) are either commercially available or can be produced according to methods known to those skilled in the art.

Suitable reaction media are those described above.

The bases and reducing agents that may be used in the process are those described above.

This enantioselective method for the preparation of compounds of general formula (S)-(I) is illustrated in scheme 9:

Scheme 9

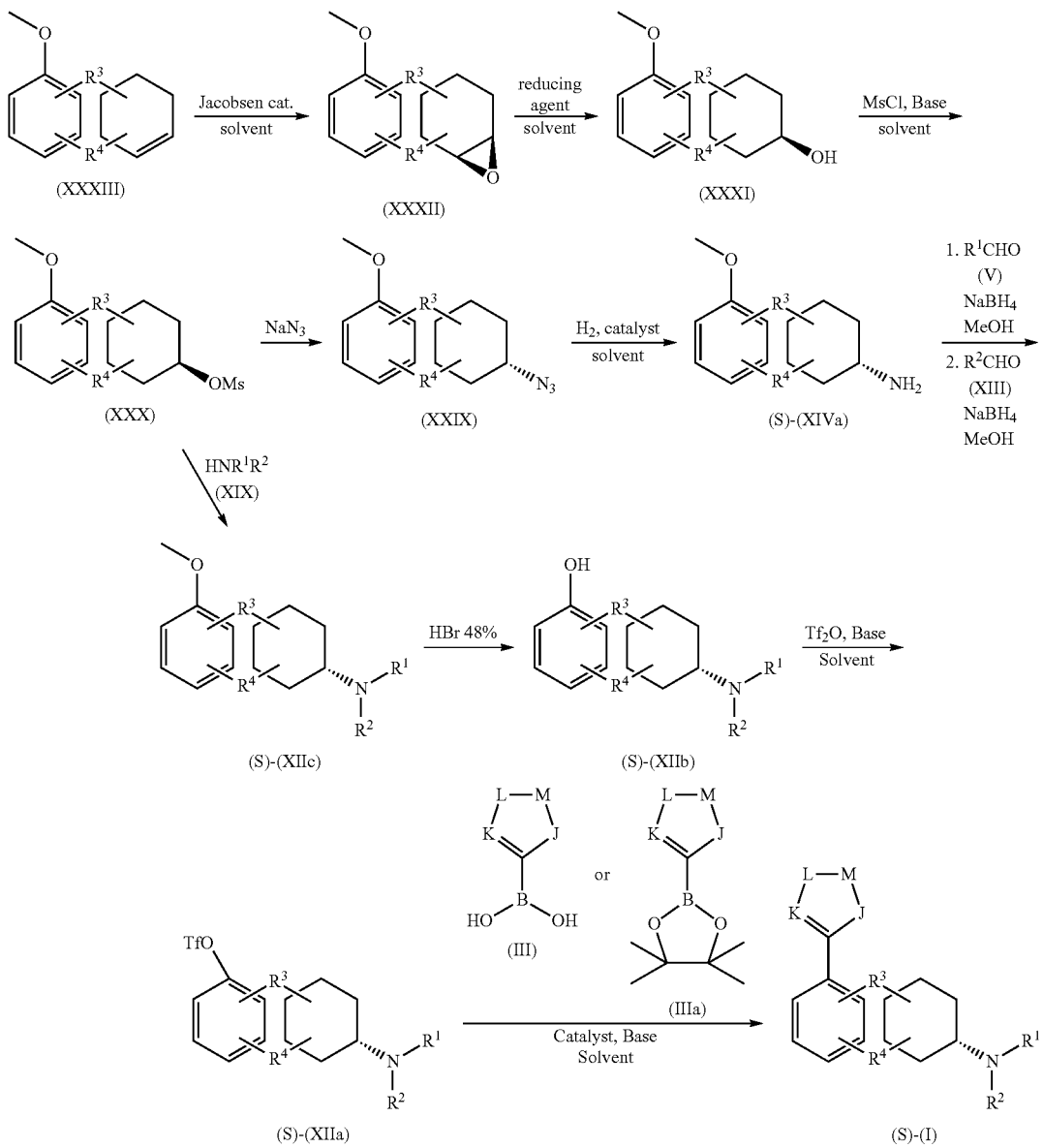

Chiral secondary alcohols of general formula (XXXI) can also be prepared by other methods known to those skilled in the art. These methods include enzymatic catalysis and transfer hydrogenation. A synthetic procedure of transfer hydrogenation is depicted in Scheme 10. According to this process, methoxy-tetralones of general formula (XXXIV),

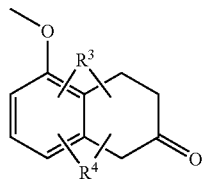

(XXXIV)

wherein $R^3$ and $R^4$ have the meaning described above, are subjected to asymmetric reduction in the presence of a chiral ligand, a suitable catalyst, 2-propanol as hydrogen source and at least one base to yield chiral alcohols of general formula (XXXI).

Target compounds of general formula (S)-(I) are obtained after several chemical transformations of compounds of general formula (XXXI) as described above (scheme 9).

Compounds of general formula (R)-(XXXI) can also be obtained following this process by using the suitable chiral ligand in the asymmetric reduction of methoxy-tetralones of general formula (XXXIV). Compounds of general formula (R)-(I) are obtained after several chemical transformations of compounds of general formula (R)-(XXXI) as described in scheme 9.

Tetralones of general formulas (XXXIV) are either commercially available or can be produced according to methods known to those skilled in the art.

Suitable reaction media are those described above.

The bases and reducing agents that may be used in the process are those described above.

This alternative enantioselective method for the preparation of compounds of general formula (S)-(I) is illustrated in scheme 10:

Scheme 10

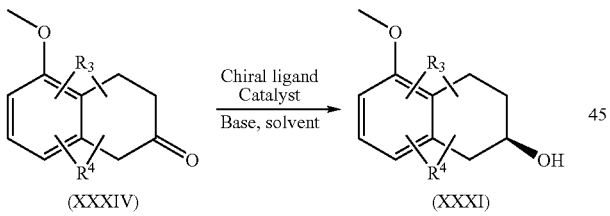

Chiral amines of general formula (S)-(XIVa) can also be prepared by asymmetrically induced reduction of a chiral imine formed from a chiral amino auxiliary as depicted in scheme 11. According to this process, compounds of general formula (XXXV), (XXXV)

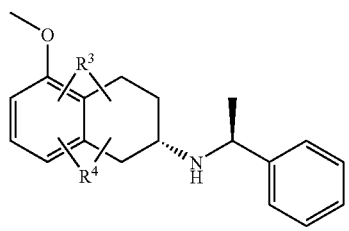

wherein $R^3$ and $R^4$ have the meaning described above, are subjected to hydrogenation in the presence of a suitable catalyst to afford chiral amines of general formula (S)-(XIVa), (S)-(XIVa)

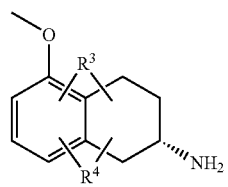

wherein $R^3$ and $R^4$ have the meaning described above. Amines of general formula (S)-(XIVa) are intermediate compounds in the synthesis of target compounds of general formula (S)-(I), which can be prepared following the processes described in schemes 5B and 9.

Compounds of general formula (XXXV) are obtained through reduction of chiral imines of general formula (XXXVI), (XXXVI)

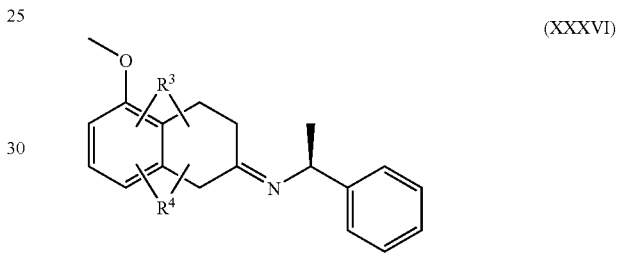

wherein $R^3$ and $R^4$ have the meaning described above.

Chiral imines of general formula (XXXVI) are prepared by amination reaction of methoxy-tetralones of general formula (XXXIV), (XXXIV)

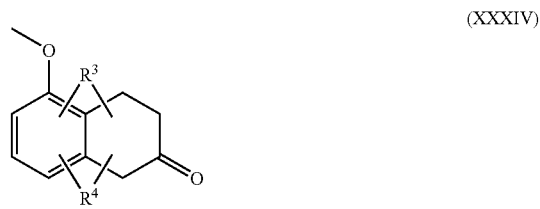

wherein $R^3$ and $R^4$ have the meaning described above, with chiral benzylmethylamine.

Tetralones of general formulas (XXXIV) are either commercially available or can be produced according to methods known to those skilled in the art.

Suitable reaction media are those described above.

The bases and reducing agents that may be used in the process are those described above.

This alternative enantioselective method for the preparation of intermediate compounds of general formula (S)-(XIVa) is illustrated in scheme 11:

Scheme 11

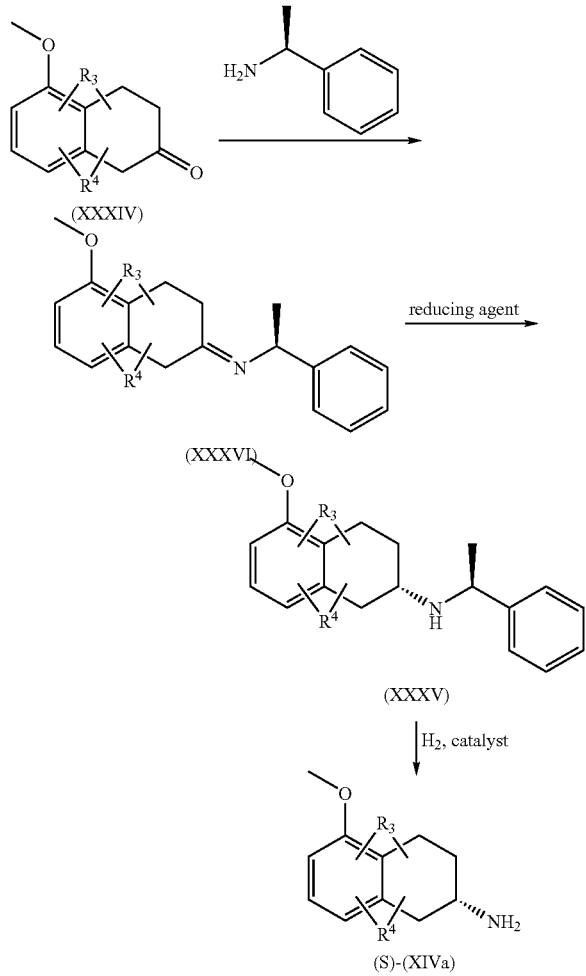

Chiral intermediates of general formula (S)-(XIIc) can also be prepared by asymmetric hydrogenation of enamines of general formula (XXXVII) as depicted in scheme 12. This reaction can be performed in the presence of a chiral ligand, a suitable catalyst, 2-propanol as hydrogen source and at least one base. Compounds of general formula (S)-(XIIc) can lead to target compounds of general formula (S)-(I), following the processes described in schemes 5B and 9.

Compounds of general formula (R)-(XIIc) can also be obtained following this process by using the suitable chiral ligand in the asymmetric hydrogenation of enamines of general formula (XXXVII). Compounds of general formula (R)-(I) are obtained after several chemical transformations of intermediate amines of general formula (R)-(XIIc) as described in schemes 5B and 9.

According to the process described in scheme 12, enamines of general formula (XXXVII),

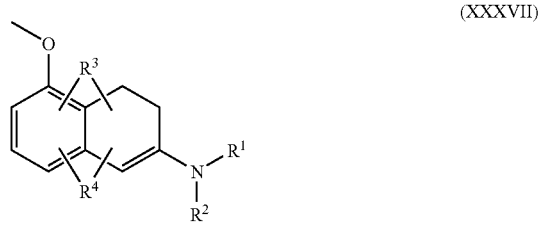

(XXXVII)

wherein $R^1$, $R^2$, $R^3$ and $R^4$ have the meaning described above, are obtained from methoxy-tetralones of general formula (XXXIV),

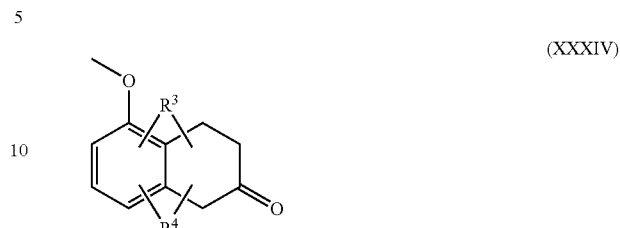

(XXXIV)

wherein $R^3$ and $R^4$ have the meaning described above, through amination reaction with secondary amines of general formula (XIX), $$HNR^1R^2 \quad (XIX)$$

wherein $R^1$ and $R^2$ have the meaning given above.

Compounds of general formulas (XXXIV) and (XIX) are either commercially available or can be produced according to methods known to those skilled in the art.

Suitable reaction media are those described above.

This enantioselective method for the preparation of intermediate compounds of general formula (S)-(XIIc) is illustrated in scheme 12:

Scheme 12

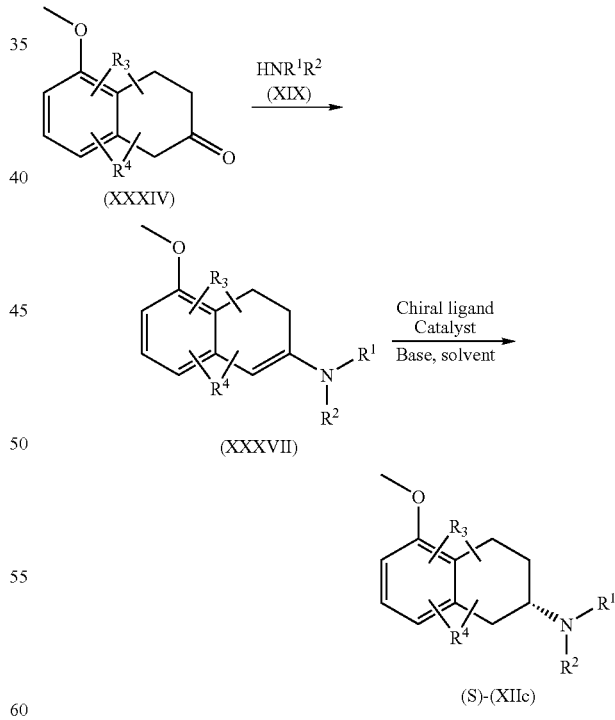

An alternative method to prepare intermediate amines of general formula (S)-(XIVa) in an enantioselective manner is illustrated in scheme 13. According to this process, desacetylation reaction of compounds of general formula (XXXVIII), (XXXVIII)

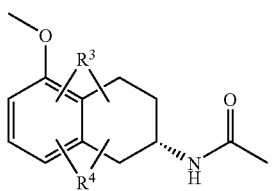

wherein R³ and R⁴ have the meaning described above, affords compounds of general formula (S)-(XIVa). Target compounds of general formula (S)-(I) can be obtained from amines of general formula (S)-(XIVa) following the processes described in schemes 5B and 9.

Enantiopure acetamides of general formula (XXXVIII) are prepared by asymmetric hydrogenation of enamides of general formula (XXXIX), (XXXIX)

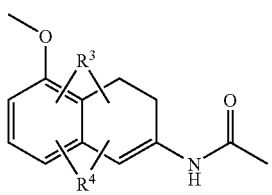

wherein R³ and R⁴ have the meaning described above. This reaction can be performed in the presence of a chiral ligand, a suitable catalyst, 2-propanol as hydrogen source and at least one base.

Compounds of general formula (R)-(XIVa) can also be obtained following this process by using the suitable chiral ligand in the asymmetric hydrogenation of enamides of general formula (XXXIX). Compounds of general formula (R)-(I) are obtained after several chemical transformations of intermediate amines of general formula (R)-(XIVa) as described in schemes 5B and 9.

Enamides of general formula (XXXIX) can be prepared from methoxy-tetralones of general formula (XXXIV) by a method that involves a phosphine-mediated reductive acylation of the preformed oxime, as described by Zhao, H. et al (Zhao, H.; Vandenbossche, C. P.; Koenig, S. G.; Singh, S. P; Bakale, R. P. *Organic Letters*, 2008, 10, 505-507). Compounds of general formula (XXXIX) can also be obtained by other methods known to those skilled in the art.

Tetralones of general formulas (XXXIV) are either commercially available or can be produced according to methods known to those skilled in the art.

Suitable reaction media and the bases that may be used in the process are those described above.

This alternative enantioselective method for the preparation of intermediate compounds of general formula (S)-(XIVa) is illustrated in scheme 13:

Scheme 13

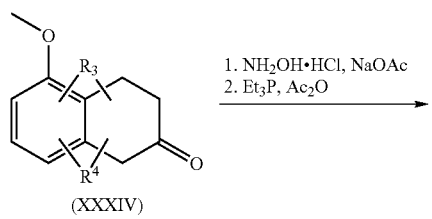

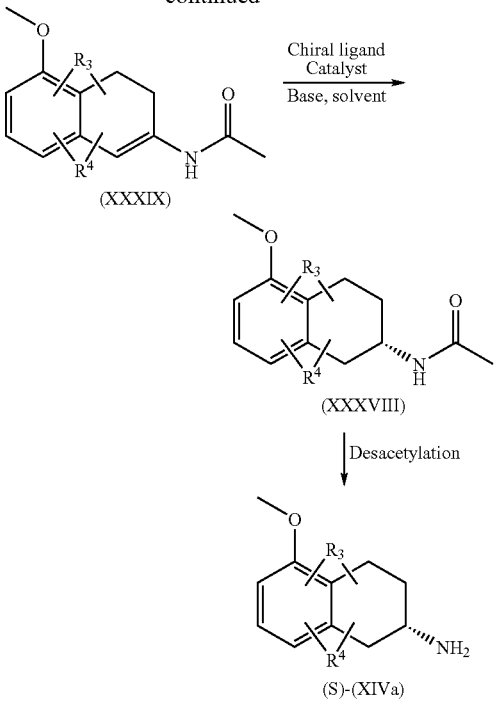

In a further aspect the present invention also provides a process for the preparation of salts of compounds of general formula (I) or (Ia), wherein at least one compound of general formula (I) or (Ia) is reacted with an inorganic and/or organic acid, preferably in the presence of a suitable reaction medium. Suitable reaction media are the ones given above. Suitable inorganic acid are for example hydrochloric acid, hydrobromic acid, phosphoric acid, sulphuric acid, nitric acid. Suitable organic acids are e.g. citric acid, maleic acid, fumaric acid, tartaric acid or derivatives thereof, such as p-toluenesulfonic acid, methanesulfonic acid or camphersulfonic acid.

In yet a further aspect the present invention also provides a process for the preparation of salts of compounds of general formula (I) or (Ia), wherein at least one compound of general formula (I) or (Ia) having at least one acidic group is reacted with one or more suitable bases, preferably in the presence of suitable reaction medium. Suitable bases are e.g. hydroxides. Carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or linear $C_{1-4}$ alkyl radical.

Solvates, preferably hydrates, of the phenylamino-substituted piperidine compounds of general formula (I) or (Ia), or corresponding stereoisomers, or corresponding salts may also be obtained by standard procedures known to those skilled in the art.

If the compounds of general formula (I) or (Ia) are obtained in form of a mixture of stereoisomers, particularly enantiomers or diastereomers, said mixtures may be separated by standard procedures known to those skilled in the art, e.g. chromatographic methods of crystallization with chiral reagents.

The purification and isolation of the phenylamino-substituted piperidine compounds of general formula (I) or (Ia) or a corresponding stereoisomer, or a corresponding salt, or corresponding solvate respectively, if required may be carried out by conventional methods known to those skilled in the art, e.g. chromatographic methods or recrystallization.

The compounds of general formula (I) or (Ia), their stereoisomers or the respective salts or solvates are toxicologically acceptable and are therefore suitable as pharmaceutical active substances for the preparation of medicaments.

The present invention therefore also provides for a medicament comprising at least one compound of general formula (I) or (Ia), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, and optionally one or more pharmaceutically acceptable adjuvants.

Furthermore, the present invention also provides for a pharmaceutical composition comprising at least one compound of general formula (I) or (Ia), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants, which is not yet formulated into a medicament.

Preferably the medicament is suitable for the regulation of a 5-$HT_7$ mediated disease or condition.

The present invention also provides for the use of at least one compound of general formula (I) or (Ia) according to the invention, optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, for the manufacture of a medicament for the treatment of a 5-$HT_7$ mediated disease or condition.

In a preferred embodiment the disease (or condition) is pain, preferably visceral pain, chronic pain, cancer pain, migraine, acute pain or neuropathic pain, more preferably neuropathic pain, allodynia or hyperalgesia.

In a preferred embodiment the disease (or condition) is sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The medicament may be in any form suitable for the application to humans and/or animals, preferably mammals, and can be produced by standard procedures known to those skilled in the art. The composition of the medicament may vary depending on the route of administration.

The medicament of the present invention may e.g. be administered parentally in combination with conventional injectable liquid carriers, such as water or suitable alcohols. Conventional pharmaceutical adjuvants for injection, such as stabilizing agents, solubilizing agents, and buffers, may be included in such injectable compositions. These medicaments may preferably be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing e.g. edible oils. Such liquid compositions may be conveniently encapsulated in e.g., gelatin capsules in a unit dosage amount.

The compositions of the present invention may also be administered topically or via a suppository.

The above mentioned compositions include preferably 1 to 60% by weight of one or more of the compound of general formula (I) or (Ia), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and 40 to 99% by weight of the appropriate pharmaceutical vehicle(s).

The daily dosage for humans and animals may vary depending on factors that have their basis in the respective species or other factors, such as age, weight or degree of illness and so forth. The daily dosage for mammals including humans usually ranges from 1 milligram to 2000 milligram, preferably 1 to 1500 mg, more preferably 1 to 1000 mg of substance to be administered during one or several intakes.

Pharmacological Methods:
Radioligand Binding

Radioligand binding assays were performed using the Cloned Human Serotonin Receptor, Subtype 7 (h5$HT_7$), expressed in CHO cells, coated on Flashplate (Basic FlashPlate Cat.: SMP200) from PerkinElmer (Cat.: 6120512). The protocol assay was essentially the recommended protocol in the Technical Data Sheet by PerkinEmer Life and Analytical Sciences. The Mass membrane protein/well was typically 12 µg and the Receptor/well was about 9-10 fmoles. The Flashplate were let equilibrate at room temperature for one hour before the addition of the components of the assay mixture. The binding buffer was: 50 mM Tris-HCl, pH 7.4, containing 10 mM $MgCl_2$, 0.5 mM EDTA and 0.5% BSA. The radioligand was [$^{125}$I]LSD at a final concentration of 0.82 nM. Nonspecific binding was determined with 50 µM of Clozapine. The assay volume was 25 µl. TopSeal-A were applied onto Flashplate microplates and they were incubated at room temperature for 240 minutes in darkness. The radioactivity were quantified by liquid scintillation spectrophotometry (Wallac 1450 Microbeta Trilux) with a count delay of 4 minutes prior to counting and a counting time of 30 seconds per well. Competition binding data were analyzed by using the LIGAND program (Munson and Rodbard, LIGAND: A versatile, computerized approach for characterization of ligand-binding systems. *Anal. Biochem.* 107: 220-239, 1980) and assays were performed in triplicate determinations for each point.

Functionality Assay on the 5HT7 Receptor
Measurement of cAMP Responses by Homogeneous Time Resolved Fluorescence cAMP measurements on HEK-293F cells that stably expressed human 5-HT7 receptors were performed by using a system based on Homogeneous Time Resolved Fluorescense (HTRF) (Gabriel et al., 2003). This technology allows the direct measurement of cAMP in living cells. The principle of this assay is based on competition between cAMP produced by cells and cAMP-XL665 conjugate for the binding with monoclonal anti-cAMP-cryptate conjugate. The HTRF cAMP kit from CisBio was used according to the manufacturer's directions. The experimental procedure was performed as stated below.

After overnight serum-free incubation, suspended cells (20,000 cells per well) were added to 96-well culture plates in incubation buffer composed of Ham's F12 (Gibco) plus 1 mM 3-isobutyl-1-methyl-xanthine (IBMX; Sigma) and 20 μM pargyline (Sigma). For agonist and antagonist experiments, 40 μl of cell suspension was added to each well. Two μl of either compound or vehicle was added at indicated concentrations and plates were preincubated for 10 min at room temperature after this initial compound addition. Then, 10 μl of either vehicle or 5-HT was added. After 30 min at 37° C., the reaction was stopped lysing the cells with a mixture of 25 μl of cryptate and 25 μl of XL-665 prepared in the lysis buffer supplied by the manufacturer. Plates were incubated for an additional hour at room temperature and read at 665 nm/620 nm using a RubyStar Plate reader (BMG LabTech).

REFERENCES

Gabriel D, Vernier M, Pfeifer M J, Dasen B, Tenaillon L, Bouhelal R. (2003) High throughput screening technologies for direct cyclic AMP measurement. *Assay Drug Dev. Technol.* 1 : 291-303.

The following examples are given to illustrate the present invention, but they do not limit the scope of the present invention.

EXAMPLES

Prepared according to above-described methods.

Example A

N-(5-Methoxy-1,2,3,4-tetrahydronaphthalen-2-yl)-N,N-dimethylamine

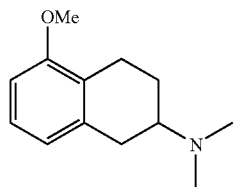

To a solution of 5-methoxy-2-tetralone (10.33 g, 58.62 mmol) dissolved in $CH_2Cl_2$ (400 mL) were added dimethylamine (5.6 M in EtOH, 14 mL, 76.206 mmol) and AcOH (0.46 mL, 5.862 mmol), and the mixture was stirred for 4 h at room temperature. It was then cooled to 0° C. and $NaB(OAc)_3H$ (0.45 eq, 5.59 g, 26.379 mmol) was added over a period of 20 min. After 1 h stirring at 0° C., $NaB(OAc)_3H$ (1.0 eq, 12.42 g, 58.62 mmol) was added over a period of 30 min. The reaction mixture was warmed to room temperature and stirred for 16 h. The mixture was cooled again to 0° C., and $H_2O$ (250 mL) was added slowly. The pH of the solution was adjusted to 8.0 by adding $NaHCO_3$ saturated aqueous solution, and the mixture was stirred at 0° C. for 15 min. The layers were separated, and the aqueous phase was extracted with $CH_2Cl_2$ (4×100 mL). All organic phases were combined, dried over anhydrous $Na_2SO_4$ and concentrated in vacuo. The residue (12.51 g) was purified by flash chromatography on silica gel (1:100:1-100:0:1 AcOEt/Hexane/$Et_3N$) affording 8.86 g of the title compound (Rf=0.5 (AcOEt/Hexane/$Et_3N$ 10:10:2), brown colored oil, 74% yield).

$^1$H-NMR (CDCl$_3$, 250 MHz, δ): 7.09 (m, 1H, ArH); 6.72 (d, J=7.4 Hz, 1H, ArH); 6.65 (d, J=8.0 Hz, 1H, ArH); 3.81 (s, 3H, CH$_3$); 2.90-3.04 (m, 2H, CH$_2$); 2.70-2.81 (m, 1H, CH); 2.47-2.64 (m, 2H, CH$_2$); 2.37 (m, 6H, CH$_3$); 2.10-2.30 (m, 1H, CH); 1.48-1.64 (m, 1H, CH)

Example B 6-(Dimethylamino)-5,6,7,8-tetrahydronaphthalen-1-ol

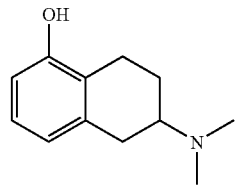

N-(5-Methoxy-1,2,3,4-tetrahydronaphthalen-2-yl)-N,N-dimethylamine (8.86 g, 43.156 mmol) was dissolved in $CH_2Cl_2$ (200 mL), cooled to 0° C. and BBr$_3$ (1.0 M in $CH_2Cl_2$, 51.8 mL, 51.788 mmol) was added over a period of 20 min. The reaction mixture was allowed to reach r.t. while stirring overnight (ca. 14 h). The mixture was cooled again to 0° C., NH$_3$ aq. (25%, 50 mL) was added slowly and the mixture was stirred at 0° C. for 15 min. The salts were filtered off, layers were separated and the aqueous phase was extracted with $CH_2Cl_2$ (4×40 mL). All organic phases were combined, dried over anhydrous Na$_2$SO$_4$ and concentrated in vacuo. The residue (6.99 g) was purified by flash chromatography on silica gel (30:70:2-100:0:2 AcOEt/Hexane/$Et_3N$ and 30:70:2 AcOEt/Hexane/$Et_3N$-90:10:2 AcOEt/MeOH/$Et_3N$) affording 2.80 g of the title compound (Rf=0.3 (AcOEt/Hexane/$Et_3N$ 10:10:2), off-white solid, 34% yield).

$^1$H-NMR (CDCl$_3$, 250 MHz, δ): 6.99 (m, 1H, ArH); 6.68 (d, J=7.6 Hz, 1H, ArH); 6.58 (d, J=7.6 Hz, 1H, ArH); 2.76 (m, 2H, CH$_2$); 2.58 (m, 2H, CH$_2$); 2.39 (s, 6H, CH$_3$); 2.17 (m, 2H, CH$_2$); 1.61 (m, 1H, CH).

Example C

N-Benzyl-N-(5-methoxy-1,2,3,4-tetrahydronaphthalen-2-yl)amine

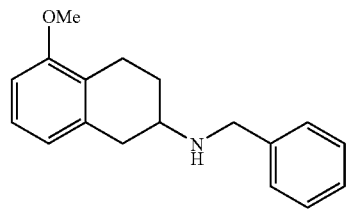

To a solution of 5-methoxy-2-tetralone (30 g, 170.24 mmol) dissolved in $CH_2Cl_2$ (250 mL) were added benzylamine (23 mL, 212.80 mmol) and AcOH (0.97 mL, 17.02 mmol), and the mixture was stirred for 4 h at room temperature. It was then cooled to 0° C. and $NaB(OAc)_3H$ (0.38 eq, 13.71 g, 64.69 mmol) was added over a period of 20 min. After 1 h stirring at 0° C., $NaB(OAc)_3H$ (1.07 eq, 38.61 g, 182.16 mmol) was added over a period of 30 min. It was added $CH_2Cl_2$ (100 mL), the reaction mixture warmed to room temperature and stirred for 15 h. The mixture was cooled again to 0° C., and H₂O (200 mL) was added slowly. The pH of the solution was adjusted to 8.0 by adding NaHCO₃ saturated aqueous solution (300 mL), and the mixture was stirred at 0° C. for 15 min. The layers were separated, and the aqueous phase was extracted with CH₂Cl₂ (2×150 mL). All organic phases were combined, dried over anhydrous Na₂SO₄ and concentrated in vacuo. The residue (58.7 g) was purified by flash chromatography on silica gel (40:60:1-100:0:1 AcOEt/Hexane/Et₃N), followed by trituration with hexane, affording 33.87 g of the title compound (Rf=0.5 (10% MeOH/CH₂Cl₂), yellow solid, 74% yield).

¹H-NMR (CDCl₃, 250 MHz, δ): 7.26-7.12 (m, 5H, ArH); 7.00 (dd, J=8.0 y 7.7 Hz, 1H, ArH); 6.60 (m, 2H, ArH); 3.82 (s, 2H, CH₂); 3.72 (s, 3H, CH₃); 2.88 (m, 2H, CH₂); 2.51 (m, 2H, CH₂); 1.99 (m, 1H, CH); 1.48 (m, 2H, CH₂).

Example D

N-Benzyl-N-[(2R)-5-methoxy-1,2,3,4-tetrahydronaphthalen-2-yl]amine

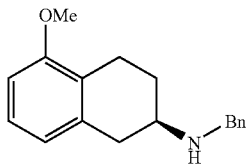

N-Benzyl-N-(5-methoxy-1,2,3,4-tetrahydronaphthalen-2-yl)amine (25.0 g, 93.507 mmol) was dissolved in Et₂O (800 mL). The reaction mixture was warmed up to reflux and (R)-(−)-mandelic acid (14.23 g, 93.507 mmol) was added. It was added CH₂Cl₂ (360 mL), and the mixture was refluxed for 2 h. The mixture was then cooled at room temperature and stirred for 15 h. The resulting solid was filtered, washed with Et₂O (3×40 mL) and dried to give 9.34 g of the diastereoisomeric salt as a white solid. The diastereoisomeric salt was recrystallized from Et₂O to improve the ee. The salt was suspended in AcOEt (300 mL), and K₂CO₃ aqueous solution (20%, 100 mL) was added. The mixture was stirred at room temperature for 2.5 h and the layers were separated. The organic phase was dried over anhydrous Na₂SO₄ and concentrated in vacuo, affording 6.0 g of the title compound (Rf=0.5 (10% MeOH/CH₂Cl₂), white solid, 24% yield).

¹H-NMR (CDCl₃, 250 MHz, δ): 7.26-7.12 (m, 5H, ArH); 7.00 (dd, J=8.0 y 7.7 Hz, 1H, ArH); 6.60 (m, 2H, ArH); 3.82 (s, 2H, CH₂); 3.72 (s, 3H, CH₃); 2.88 (m, 2H, CH₂); 2.51 (m, 2H, CH₂); 1.99 (m, 1H, CH); 1.48 (m, 2H, CH₂)

Example E (6R)-6-[Benzyl(methyl)amino]-5,6,7,8-tetrahydronaphthalen-1-ol

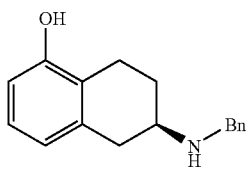

N-Benzyl-N-[(2R)-5-methoxy-1,2,3,4-tetrahydronaphthalen-2-yl]amine (10.0 g, 37.40 mmol) was suspended in HBr aq. (48%, 250 mL), and the reaction mixture was refluxed for 4 h. The mixture was allowed to reach room temperature, and it was then cooled to −78° C. The pH of the solution was adjusted to 9.0 by adding NH₃ aqueous solution (25%). The mixture was allowed to reach room temperature, and was stirred for 30 min. The aqueous phase was extracted with AcOEt (2×300 mL). All organic phases were combined, dried over anhydrous Na₂SO₄ and concentrated in vacuo to afford 9.4 g of the title compound (Rf=0.4 (10% MeOH/CH₂Cl₂), white solid, 99% yield).

¹H-NMR (CDCl₃, 250 MHz, δ): 9.13 (sa, 1H, OH); 7.38-7.17 (m, 5H, ArH); 6.86 (m, 1H, ArH); 6.54 (d, J=8.0 Hz, 1H, ArH); 6.47 (d, J=7.4 Hz, 1H, ArH); 3.80 (s, 2H, CH₂); 2.92-2.67 (m, 2H, CH₂); 2.41 (m, 2H, CH₂); 2.00 (m, 1H, CH); 1.45 (m, 2H, CH₂).

Example F (6R)-6-Amino-5,6,7,8-tetrahydronaphthalen-1-ol

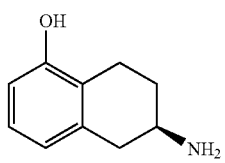

A solution of (6R)-6-[Benzyl(methyl)amino]-5,6,7,8-tetrahydronaphthalen-1-ol (4.80 g, 18.946 mmol) in THF (150 mL) was added to Pd/C (1.90 g, 10% weight of Pd on activated carbon), and the reaction mixture was stirred under H₂ (g) atmosphere for 16 h. It was filtered through Celite washing with AcOEt (1×200 mL) and the solvent was concentrated off to afford 3.0 g of the title product (Rf=0.1 (20% MeOH/CH₂Cl₂), off-white solid, 97% yield).

¹H-NMR (CDCl₃, 250 MHz, δ): 6.99 (m, 1H, ArH); 6.61 (dd, J=7.4, 8.2 Hz, 1H, ArH); 3.18 (m, 1H, CH); 3.02-2.82 (m, 2H, CH₂); 2.70-2.52 (m, 2H, CH₂); 2.05 (m, 1H, CH); 1.24 (m, 1H, CH)

Example G (6R)-6-(Dimethylamino)-5,6,7,8-tetrahydronaphthalen-1-ol

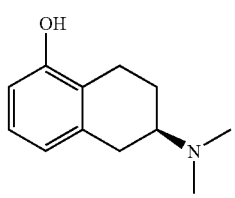

Formaldehyde (10 mL 37% aqueous solution, 133.481 mmol) was added to a solution of (6R)-6-Amino-5,6,7,8-tetrahydronaphthalen-1-ol (3.0 g, 18.38 mmol) in MeOH (100 mL) and THF (15 mL). The reaction mixture was stirred at room temperature for 15 min, and NaBH₄ (2.0 g, 52.868 mmol) was added. The reaction mixture was stirred at room temperature for 2 h, poured into H₂O (300 mL) and extracted with CH₂Cl₂ (2×300 mL). The organic layer was dried over anhydrous Na₂SO₄, filtered and concentrated. The product was purified by flash chromatography on silica gel (0-5-10-

15-20% Et₃N/AcOEt) to furnish 2.74 g of the title product (Rf=0.5 (20% Et₃N/AcOEt), off-white solid, 78% yield).

¹H-NMR (CDCl₃, 250 MHz, δ): 6.99 (m, 1H, ArH); 6.68 (d, J=7.6 Hz, 1H, ArH); 6.58 (d, J=7.6 Hz, 1H, ArH); 2.76 (m, 2H, CH₂); 2.58 (m, 2H, CH₂); 2.39 (s, 6H, CH₃); 2.17 (m, 2H, CH₂); 1.61 (m, 1H, CH)

Example H (6R)-6-(Dimethylamino)-5,6,7,8-tetrahydronaphtha-len-1-yl trifluoromethanesulfonate

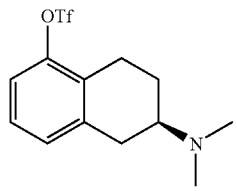

Tf₂O (4.3 mL, 25.452 mmol) was dropwise added to a −78° C. cooled solution of (6R)-6-(dimethylamino)-5,6,7,8-tetrahydronaphthalen-1-ol (4.25 g, 22.218 mmol) and Et₃N (8.0 mL, 57.396 mmol) in CH₂Cl₂ (90 mL). The reaction was completed after 5 min at low temperature. The reaction mixture was poured into brine (200 mL) and extracted with CH₂Cl₂ (2×200 mL). The organic layer was dried over anhydrous Na₂SO₄, filtered and concentrated. The crude residue was flash chromatographed on silica gel (5-10% MeOH/CH₂Cl₂) to furnish 5.10 g of the title product (Rf=0.4 (10% MeOH/CH₂Cl₂), pale brown colored oil, 71% yield).

¹H-NMR (CDCl₃, 250 MHz, δ): 7.14 (m, 3H, ArH); 3.02 (m, 2H, CH₂); 2.79 (m, 2H, CH₂); 2.60 (m, 1H, CH); 2.38 (s, 6H, CH₃); 2.18 (m, 1H, CH); 1.62 (m, 1H, CH).

Example I (2R)-Dimethyl-[5-(1,3,5-trimethyl-1H-pyrazol-4-yl)-1,2,3,4-tetrahydro-naphthalen-2-yl]-amine

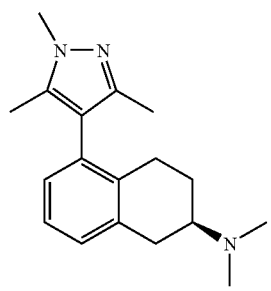

(6R)-6-(Dimethylamino)-5,6,7,8-tetrahydronaphthalen-1-yl trifluoromethanesulfonate (2.5 g, 7.731 mmol), 1,3,5-trimethyl-1H-pyrazole-4-boronic acid pinacol ester (2.10 g, 8.893 mmol) and Pd(PPh₃)₄ (1.2 g, 1.038 mmol) were added to a solution of K₂CO₃ (2.15 g, 15.556 mmol) in a mixture of 1,2-dimethoxyethane (60 mL) and H₂O (8 mL). The reaction mixture was purged with N₂ (g) for 10 min, and warmed up to reflux. The reaction was completed in 2 h. It was allowed to reach room temperature, diluted with H₂O (200 mL) and extracted with AcOEt (1×400 mL). The organic layer was dried over anhydrous Na₂SO₄, filtered and concentrated. The residue was purified by flash chromatography on silica gel (0-10-20% Et₃N/AcOEt) to afford the desired product as a brown-colored oil. The material was dissolved in CH₂Cl₂ (200 mL) and acidified with HCl aqueous solution (6 N). The organic layer was discarded, and the aqueous layer was taken to pH>13 with NaOH aqueous solution (6 N). It was extracted with CH₂Cl₂ (3×300 mL), and the organic layer was dried over anhydrous Na₂SO₄, filtered and concentrated, to give 1.45 g of the coupling product (Rf=0.2 (10% Et₃N/AcOEt), colorless oil, 66% yield).

¹H-NMR (CDCl₃, 250 MHz, δ): 7.16-7.06 (m, 2H, ArH); 6.90 (m, 1H, ArH); 3.77 (d, 3H, J=1.4 Hz, CH₃); 3.02 (m, 1H, CH); 2.83 (m, 1H, CH); 2.68-2.28 (m, 4H, CH₂); 2.37 (s, 6H, CH₃); 2.04 (s, 3H, CH₃); 2.00 (d, J=2.7 Hz, 3H, CH₃); 1.51 (m, 1H, CH)

Example J (2R)-Dimethyl-[5-(1,3,5-trimethyl-1H-pyrazol-4-yl)-1,2,3,4-tetrahydro-naphthalen-2-yl]-amine dihydrochloride

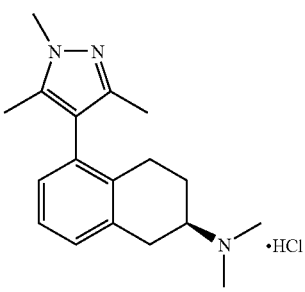

HCl (9.2 mL, 4 M solution in dioxane, 18.51 mmol) was dropwise added to a suspension of (2R)-dimethyl-[5-(1,3,5-trimethyl-1H-pyrazol-4-yl)-1,2,3,4-tetrahydro-naphthalen-2-yl]amine (1.75 g, 6.17 mmol) in Et₂O (10 mL). The reaction mixture was stirred at room temperature for 3 h and then the solvent was concentrated off. The resulting solid was suspended in Et₂O (25 mL) and concentrated, in order to remove excess of HCl. This operation was done for three times, to give 1.95 g of the title product (Rf=0.2 (10% Et₃N/AcOEt), white solid, 99% yield).

¹H NMR (250 MHz, DMSO-d₆) δ ppm 1.74 (m, 1H) 2.01 (d, J=5.08 Hz, 3H) 2.05 (d, J=5.08 Hz, 3H) 2.24 (d, J=12.08 Hz, 1H) 2.44 (m, 2H) 2.74 (s, 3H) 2.76 (s, 3H) 3.00-3.31 (m, 2 H) 3.58 (br. s., 1H) 3.84 (s, 3H) 6.96 (t, J=5.49 Hz, 1H) 7.10-7.28 (m, 2H). MS-EI+ m/z: 283.21 (M-HCl)

Example L (2S)-[5-(3,5-Dimethyl-1H-pyrazol-4-yl)-1,2,3,4-tetrahydro-naphthalen-2-yl]-dimethyl-amine dihydrochloride

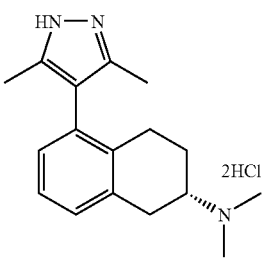

(6S)-6-(Dimethylamino)-5,6,7,8-tetrahydronaphthalen-1-yl trifluoromethanesulfonate (231 mg, 0.71 mmol), 3,5-dimethylpyrazole-4-boronic acid pinacol ester (206 mg, 0.93 mmol) and Pd(PPh₃)₄ (82 g, 0.0714 mmol) were added to a solution of K₂CO₃ (197 mg, 1.43 mmol) in a mixture of 1,2-dimethoxyethane (7.5 mL) and H₂O (1 mL). The reaction mixture was purged with Ar (g) for 10 min, and warmed up to reflux. The reaction was completed in 5.5 h. It was allowed to reach room temperature, diluted with CH$_2$Cl$_2$ (10 mL) and acidified with HCl aqueous solution (10%, 20 mL). The organic layer was discarded, and the aqueous layer was taken to pH=9-10 with NaOH aqueous solution (10%). It was extracted with CH$_2$Cl$_2$ (3×10 mL), and the organic layer was dried over anhydrous Na$_2$SO$_4$, filtered and concentrated. The residue was purified by flash chromatography on silica gel (CH$_2$Cl$_2$/MeOH/NH$_3$ (7.0 M en MeOH) 95:5:1-50:50:50), to afford the base of the desired product (yellow oil, 67% yield).

Then, HCl (0.750 mL, 2 M solution in Et$_2$O, 1.5 mmol) was dropwise added to a suspension of (2S)-[5-(3,5-Dimethyl-1H-pyrazol-4-yl)-1,2,3,4-tetrahydro-naphthalen-2-yl]-dimethyl-amine (129 mg, 0.48 mmol) in Et$_2$O (5 mL). The reaction mixture was stirred at room temperature for 5 h and then the solvent was concentrated off. The resulting solid was suspended in Et$_2$O (5 mL) and concentrated, in order to remove excess of HCl. This operation was done for three times, to give 119 mg of the title product (white solid, 81% yield).

Example AB (2S)-Isopropyl-methyl-[5-(1,3,5-trimethyl-1H-pyrazol-4-yl)-1,2,3,4-tetrahydro-naphthalen-2-yl]-amine

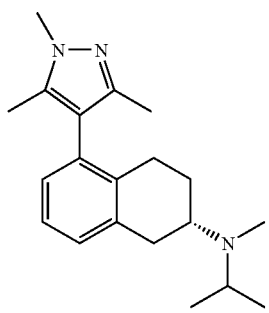

(S)-6-(Isopropyl(methyl)amino)-5,6,7,8-tetrahydronaphthalen-1-yl trifluoromethanesulfonate (184 mg, 0.524 mmol), 1,3,5-trimethyl-1H-pyrazole-4-boronic acid pinacol ester (142 mg, 0.602 mmol) and Pd(PPh$_3$)$_4$ (60 g, 0.0524 mmol) were added to a solution of K$_2$CO$_3$ (145 mg, 1.047 mmol) in a mixture of 1,2-dimethoxyethane (7 mL) and H$_2$O (1 mL). The reaction mixture was purged with Ar (g) for 10 min, and warmed up to reflux. The reaction was completed in 4 h. It was allowed to reach room temperature, diluted with CH$_2$Cl$_2$ (20 mL) and acidified with HCl aqueous solution (10%, 30 mL). The organic layer was discarded, and the aqueous layer was taken to pH=9-10 with NaOH aqueous solution (10%). It was extracted with CH$_2$Cl$_2$ (3×20 mL), and the organic layer was dried over anhydrous Na$_2$SO$_4$, filtered and concentrated. The obtained crude was purified by flash chromatography on silica gel (5% Et$_3$N/AcOEt), to afford 91 mg of the desired product (yellow oil, 56% yield).

$^1$H NMR (250 MHz, DMSO-d$_6$) δ ppm 7.10 (m, 2H), 6.89 (m, 1H), 3.77 (s, 3H), 3.16-2.83 (m, 4H), 2.65-2.32 (m, 2H), 2.27 (s, 3H), 2.03 (s, 3H), 2.02 (s, 3H), 1.9 (m, 1H), 1.58 (m, 1H), 1.07 (d, J=6.0 Hz, 6H).

Compounds of General Formula (S)-(XXXI)
(2S)-5-Methoxy-2-tetralol

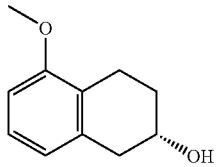

First Step: Jacobsen Epoxidation

To a solution of 8-methoxy-1,2-dihydronaphthalene (2.92 g, 18.2 mmol) in dichloromethane (1.2 L) was added 4-phenylpyridine-N-oxide (311 mg, 1.82 mmol, 0.1 eq) and (R,R)-Jacobsen catalyst (290 mg, 0.455 mmol, 0.025 eq). The solution was cooled to 0° C. and a 0.576 M NaClO solution was added drop wise via addition funnel. The reaction mixture was vigorously stirred at 0-5° C. for 3 h. Then, it was filtered through a pad of Celite, dried and concentrated to yield 3.63 g of crude epoxide.

Second Step: Epoxide Reduction

To a suspension of LiAlH$_4$ (345 mg, 9.1 mmol, 0.5 eq) in dry THF (32 mL) cooled to 0° C. was added via cannula a solution of 1,2-epoxy-5-methoxy-1,2,3,4-tetrahydronaphthalene (Jacobsen crude, 18.2 mmol) in dry THF (160 mL) and it was heated at 80° C. for 2 h. The solution was left to cool down to room temperature and quenched with 3N HCl (5 mL). Then, it was extracted with diethyl ether, dried and concentrated in vacuo. After purification by flash chromatography, 1.09 g of pure 5-methoxy-2-tetralol were obtained (34% yield, two steps).

Compounds of General Formula (S)-(XXX)
(2S)-5-Methoxy-2-tetralol methanesulfonate

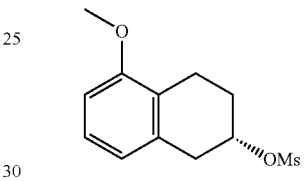

To a cooled solution of (2S)-5-methoxy-2-tetralol (700 mg, 3.93 mmol) in dry dichloromethane (4.5 mL) was added triethylamine (0.820 mL, 5.9 mmol, 1.5 eq) and methanesulfonil chloride (0.36 mL, 4.7 mmol, 1.2 eq). The resulting solution was stirred at 0° C. for 45 min. Then, it was diluted with dichloromethane, washed with saturated NaHCO$_3$ (5 mL×2) and brine, dried and evaporated. Pure methanesulfonate was obtained in quantitative yield.

$^1$H-NMR (400 MHz): 7.12 (t, 1H, J=8 Hz), 6.69 (d, 2H, J=8 Hz), 5.14 (m, 1H), 3.81 (s, 3H), 3.20 (dd, 1H, J=16 and 4 Hz), 3.07 (dt, 1H, J=16 and 7 Hz), 3.02 (s, 3H), 2.91 (dt, 1H, J=18 and 6 Hz), 2.74 (dt, 1H, J=18 and 7 Hz), 2.14 (m, 2H).

Compounds of General Formula (R)-(XXIX)
(2R)-2-Azido-5-methoxy-1,2,3,4-tetrahydronaphthalene

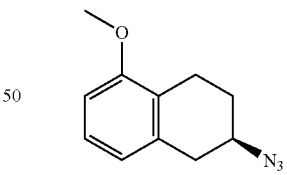

(2S)-5-methoxy-2-tetralol methanesulfonate (3.93 mmol) and sodium azide (766 mg, 11.8 mmol) were dissolved in DMF (80 mL) and heated at 50° C. overnight. Then, it was cooled down to room temperature, brine was added (120 mL) and the solution was extracted with dichloromethane (60 mL×3). The organic layer was washed with saturated NaHCO$_3$ (50 mL×2) and brine (50 mL), dried and evaporated. 717 mg of azido compound (89% yield, 2 steps) were obtained.

$^1$H-NMR (400 MHz): 7.12 (t, 1H, J=8 Hz), 6.70 (t, 2H, J=8 Hz), 3.83 (m, 1H), 3.82 (s, 3H), 2.93 (dt, 1H, J=18 and 6 Hz), 2.82 (dd, 1H, J=16 and 9 Hz), 2.66 (m, 1H), 2.14 (m, 1H), 1.84 (m, 1H).

Compounds of General Formula (S)-(XIVa)

(2R)-2-Amino-5-methoxy-1,2,3,4-tetrahydronaphthalene

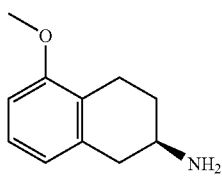

To a suspension of 67 mg of Pd/C in ethyl acetate (5 mL) under $H_2$ atmosphere, (2R)-2-azido-5-methoxy-1,2,3,4-tetrahydronaphthalene (667 mg, 3.28 mmol) in ethyl acetate (20 mL) was added via cannula. The reaction mixture was stirred overnight. Then, it was filtered through a pad of celite, washed with ethyl acetate and concentrated in vacuo to yield the amino compound in 98% yield (596 mg).

$^1$H-NMR (400 MHz): 7.09 (t, 1H, J=8 Hz), 6.70 (d, 1H, J=8 Hz), 6.66 (d, 1H, J=8 Hz), 3.81 (s, 3H), 3.17 (m, 1H), 2.95 (m, 2H), 2.60 (m, 2H), 2.04 (m, 1H) 1.80 (b, 2H), 1.77 (m, 1H).

Data of examples that were or are prepared according to the reaction schemes and descriptions given above are given in the following table:

| Example | Structure | Name | $^1$H-NMR |
|---|---|---|---|
| J | 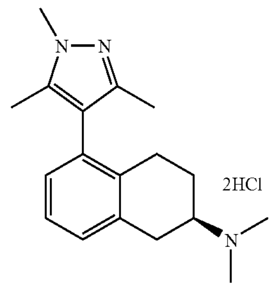 | (2R)-Dimethyl-[5-(1,3,5-trimethyl-1H-pyrazol-4-yl)-1,2,3,4-tetrahydro-naphthalen-2-yl]-amine dihydrochloride | $^1$H NMR (250 MHz, DMSO-$d_6$) δ ppm 1.74 (m, 1H), 2.01 (d, J = 5.08 Hz, 3H), 2.05 (d, J = 5.08 Hz, 3H), 2.24 (d, J = 12.08 Hz, 1H), 2.44 (m, 2H), 2.74 (s, 3H), 2.76 (s, 3H), 3.00-3.31 (m, 2H), 3.58 (br. s., 1 H), 3.84 (s, 3H), 6.96 (t, J = 5.49 Hz, 1H), 7.10-7.28 (m, 2H) |
| K | 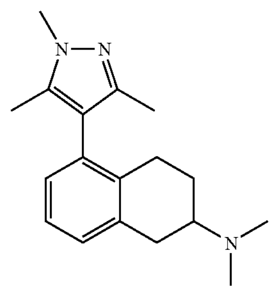 | Dimethyl-[5-(1,3,5-trimethyl-1H-pyrazol-4-yl)-1,2,3,4-tetrahydro-naphthalen-2-yl]-amine | |
| L | 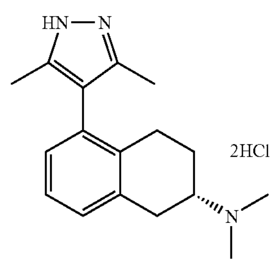 | (2S)-[5-(3,5-Dimethyl-1H-pyrazol-4-yl)-1,2,3,4-tetrahydro-naphthalen-2-yl]-dimethyl-amine dihydrochloride | $^1$H NMR (250 MHz, DMSO-$d_6$) δ ppm 11.16 (bs, 1H), 7.23 (m, 2H); 7.03 (d, J = 6.3, 1H), 3.60 (m, 1H), 3.31-3.02 (m, 2H), 2.77 (s, 3H), 2.75 (s, 3H), 2.23 (m, 1H), 2.10 (s, 3H), 2.08 (s, 3H), 1.74 (m, 1H) |
| M | 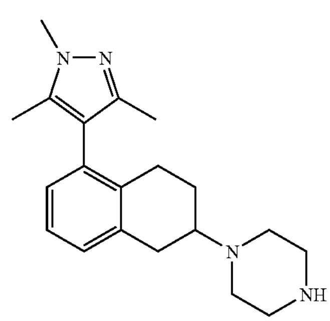 | 1-[5-(1,3,5-Trimethyl-1H-pyrazol-4-yl)-1,2,3,4-tetrahydro-naphthalen-2-yl]-piperazine | |

| Example | Structure | Name | ¹H-NMR |
|---------|-----------|------|--------|
| N | 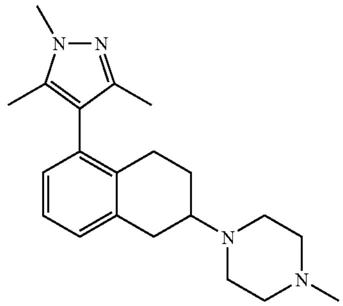 | 1-Methyl-4-[5-(1,3,5-trimethyl-1H-pyrazol-4-yl)-1,2,3,4-tetrahydro-naphthalen-2-yl]-piperazine | |
| O | 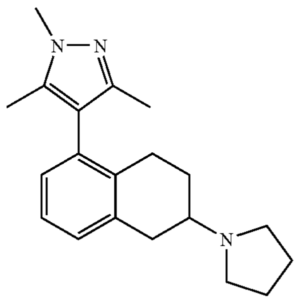 | 1,3,5-Trimethyl-4-(6-pyrrolidin-1-yl-5,6,7,8-tetrahydro-naphthalen-1-yl)-1H-pyrazole | |
| P | 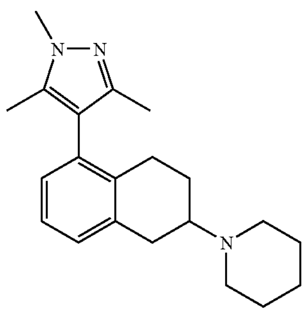 | 1-[5-(1,3,5-Trimethyl-1H-pyrazol-4-yl)-1,2,3,4-tetrahydro-naphthalen-2-yl]-piperidine | |
| Q | 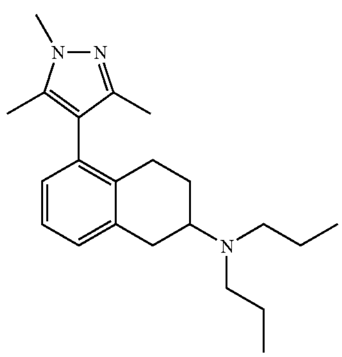 | Dipropyl-[5-(1,3,5-trimethyl-1H-pyrazol-4-yl)-1,2,3,4-tetrahydro-naphthalen-2-yl]-amine | |
| R | 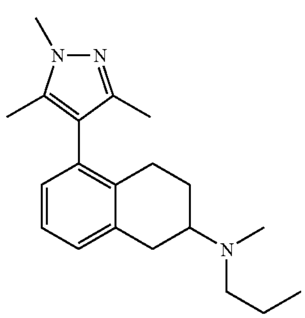 | Methyl-propyl-[5-(1,3,5-trimethyl-1H-pyrazol-4-yl)-1,2,3,4-tetrahydro-naphthalen-2-yl]-amine | |

| Example | Structure | Name | ¹H-NMR |
|---|---|---|---|
| S | 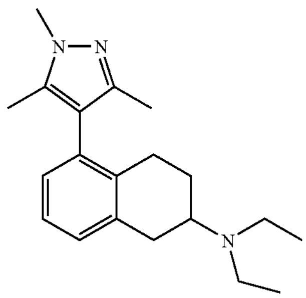 | Diethyl-[5-(1,3,5-trimethyl-1H-pyrazol-4-yl)-1,2,3,4-tetrahydro-naphthalen-2-yl]-amine | |
| T | 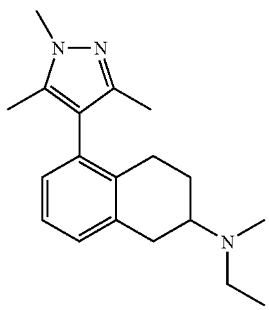 | Ethyl-methyl-[5-(1,3,5-trimethyl-1H-pyrazol-4-yl)-1,2,3,4-tetrahydro-naphthalen-2-yl]-amine | |
| U | 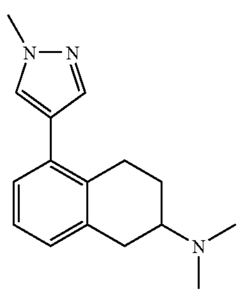 | Dimethyl-[5-(1-methyl-1H-pyrazol-4-yl)-1,2,3,4-tetrahydro-naphthalen-2-yl]-amine | |
| V | 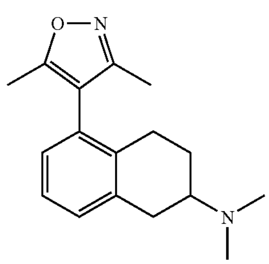 | [5-(3,5-Dimethyl-isoxazol-4-yl)-1,2,3,4-tetrahydro-naphthalen-2-yl]-dimethyl-amine | |
| W | 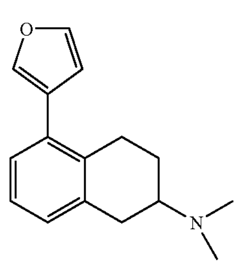 | (5-Furan-3-yl-1,2,3,4-tetrahydro-naphthalen-2-yl)-dimethyl-amine | |

-continued

| Example | Structure | Name | ¹H-NMR |
|---------|-----------|------|--------|
| X | 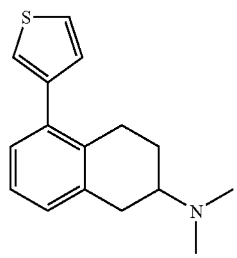 | Dimethyl-(5-thiophen-3-yl-1,2,3,4-tetrahydro-naphthalen-2-yl)-amine | |
| Y | 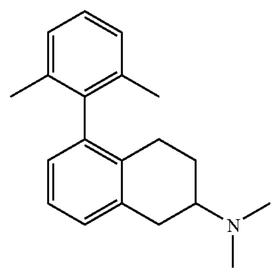 | [5-(2,6-Dimethyl-phenyl)-1,2,3,4-tetrahydro-naphthalen-2-yl]-dimethyl-amine | |
| Z | 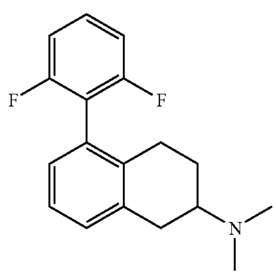 | [5-(2,6-Difluoro-phenyl)-1,2,3,4-tetrahydro-naphthalen-2-yl]-dimethyl-amine | |
| AA | 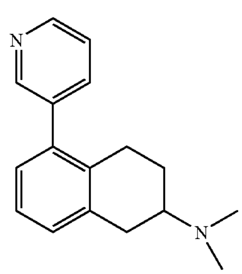 | Dimethyl-(5-pyridin-3-yl-1,2,3,4-tetrahydro-naphthalen-2-yl)-amine | |
| AB | 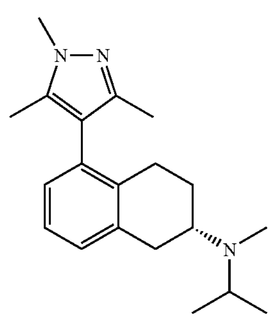 | (2S)-Isopropyl-methyl-[5-(1,3,5-trimethyl-1H-pyrazol-4-yl)-1,2,3,4-tetrahydro-naphthalen-2-yl]-amine | ¹H NMR (250 MHz, DMSO-d₆) δ ppm 7.10 (m, 2H), 6.89 (m, 1H), 3.77 (s, 3H), 3.16-2.83 (m, 4H), 2.65-2.32 (m, 2H), 2.27 (s, 3H), 2.03 (s, 3H), 2.02 (s, 3H), 1.9 (m, 1 H), 1.58 (m, 1 H), 1.07 (d, J = 6.0 Hz, 6H) |

-continued

| Example | Structure | Name | ¹H-NMR |
|---|---|---|---|
| AC | 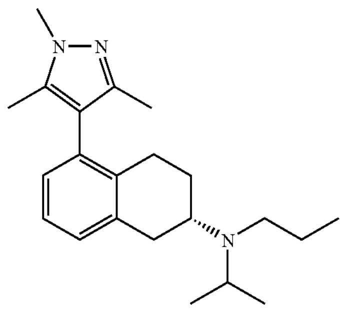 | (2S)-Isopropyl-propyl-[5-(1,3,5-trimethyl-1H-pyrazol-4-yl)-1,2,3,4-tetrahydro-naphthalen-2-yl]-amine | |
| AD | 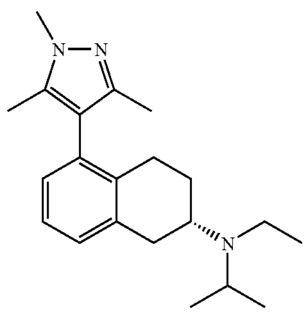 | (2S)-Ethyl-isopropyl-[5-(1,3,5-trimethyl-1H-pyrazol-4-yl)-1,2,3,4-tetrahydro-naphthalen-2-yl]-amine | |
| AE | 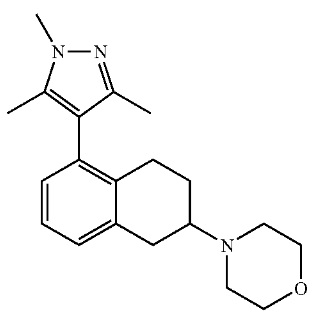 | 4-[5-(1,3,5-Trimethyl-1H-pyrazol-4-yl)-1,2,3,4-tetrahydro-naphthalen-2-yl]-morpholine | |
| AF | 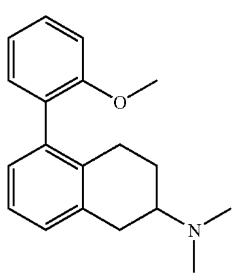 | [5-(2-Methoxy-phenyl)-1,2,3,4-tetrahydro-naphthalen-2-yl]-dimethyl-amine | |
| AG | 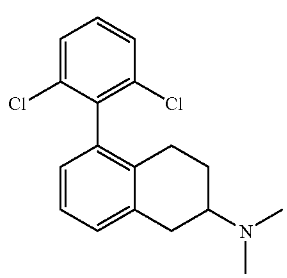 | [5-(2,6-Dichloro-phenyl)-1,2,3,4-tetrahydro-naphthalen-2-yl]-dimethyl-amine | |

| Example | Structure | Name | $^1$H-NMR |
|---|---|---|---|
| AH | 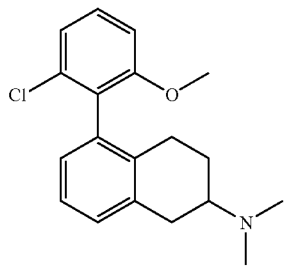 | [5-(2-Chloro-6-methoxy-phenyl)-1,2,3,4-tetrahydro-naphthalen-2-yl]-dimethyl-amine | |
| AI | 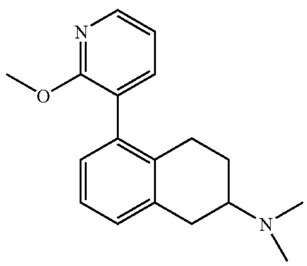 | [5-(2-Methoxy-pyridin-3-yl)-1,2,3,4-tetrahydro-naphthalen-2-yl]-dimethyl-amine | |

Pharmacological Data:

Results for representative compounds/examples are given in the table below:

| COMPOUND/ EXAMPLE | 5-HT$_7$ IC$_{50}$ (nM) | 5-HT$_7$ Ki (nM) |
|---|---|---|
| J | 178.4 | |
| K | 3.9 ± 1.7 | |
| L | 18.4 ± 2.5 | |
| O | | 96.3 ± 2 |
| R | | 9.1 ± 1.5 |
| S | | 129.8 |
| T | | 10.3 ± 0.4 |
| AB | | 644.2 ± 63.5 |
| AC | | 226.7 ± 11.3 |
| AF | | 25.8 ± 4.6 |
| AH | | 11.6 ± 3 |
| AI | | 61.6 ± 5.8 |

Formulation Example

Example of a Tablet Formulation

| | |
|---|---|
| Compound according to example K | 5 mg |
| Lactose | 60 mg |
| Crystalline cellulose | 25 mg |
| Povidone K 90 | 5 mg |
| Pregelanitized starch | 3 mg |
| Colloidal silica dioxide | 1 mg |
| Magnesium stearate | 1 mg |
| Total weight per tablet | 100 mg |

The above mentioned ingredients were mixed and compressed into a tablet by conventional methods known to those skilled in the art.

The invention claimed is:

1. Compound, or a salt thereof, of Formula Ia,

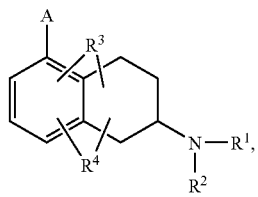

(Ia)

wherein

A is selected from the following group

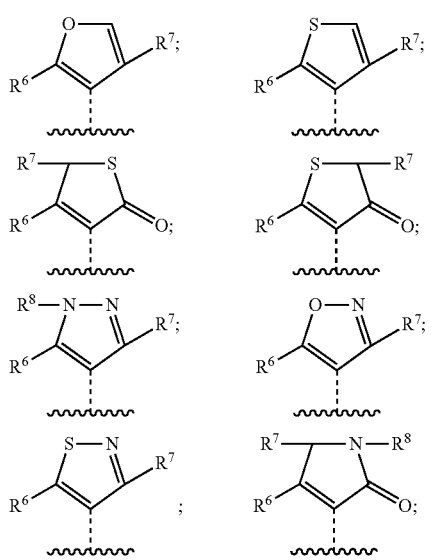

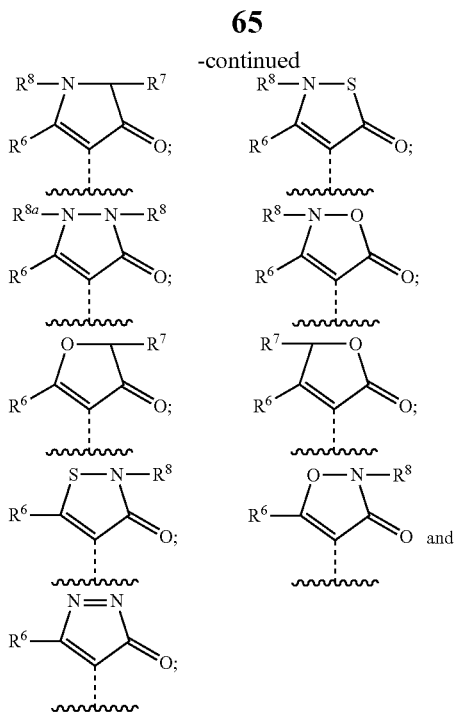

$R^1$ and $R^2$ are independently from each other a linear or branched, saturated or unsaturated, optionally at least mono-substituted aliphatic radical, or $R^1$ and $R^2$ together with their connecting nitrogen form an optionally at least mono-substituted heterocyclic ring system;

$R^3$ and $R^4$ are independently from each other selected from hydrogen; halogen; OH; SH; $NH_2$; a linear or branched, saturated or unsaturated, optionally at least mono-substituted aliphatic radical; and O—R with R being a linear or branched, saturated or unsaturated, optionally at least mono-substituted aliphatic radical;

$R^6$ and $R^7$ are independently from each other selected from hydrogen; halogen; OH; SH; $NH_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or O, with the proviso that (2S)-dimethyl-[5-(1,3,5-trimethyl-1H-pyrazol-4-yl)-1,2,3,4-tetrahydro-naphthalen-2-yl]-amine is excluded.

2. Compound, or a salt thereof, according to claim 1 of Formula Ia, wherein
A is selected from the following group

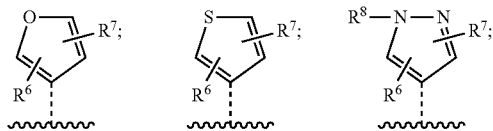

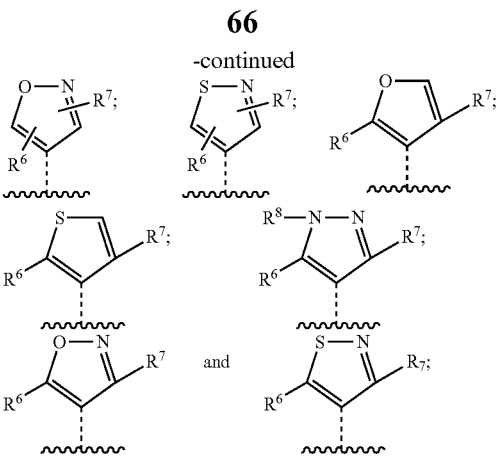

$R^1$ and $R^2$ are independently from each other a linear or branched, saturated or unsaturated, optionally at least mono-substituted aliphatic radical, or $R^1$ and $R^2$ together with their connecting nitrogen are forming an optionally at least mono-substituted heterocyclic ring system;

$R^3$ and $R^4$ are independently from each other selected from hydrogen; halogen; OH; SH; $NH_2$; a linear or branched, saturated or unsaturated, optionally at least mono-substituted aliphatic radical; and O—R with R being a linear or branched, saturated or unsaturated, optionally at least mono-substituted aliphatic radical;

$R^6$ and $R^7$ are independently from each other selected from hydrogen; halogen; OH; SH; $NH_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

$R^8$ is selected from hydrogen and an aliphatic radical, which is linear or branched, saturated or unsaturated, and optionally at least mono-substituted by F, Cl, Br, I, SH or OH.

3. Compound, or a salt thereof, according to claim 1, characterized in that $R^1$ and $R^2$ are independently from each other a linear or branched, optionally at least mono-substituted $C_{1-4}$-alkyl radical.

4. Compound, or a salt thereof, according to claim 1, characterized in that $R^1$ and $R^2$ together with their connecting nitrogen form an optionally at least mono-substituted heterocyclic ring system of 4 to 7 ring members.

5. Compound, or a salt thereof, according to claim 1, characterized in that $R^3$ and $R^4$ are independently from each other selected from hydrogen; halogen; OH; SH; $NH_2$; a linear or branched, optionally at least mono-substituted $C_{1-4}$-alkyl radical; and O—R with R being a linear or branched, optionally at least mono-substituted $C_{1-4}$-alkyl radical.

6. Compound, or a salt thereof, according to claim 1, characterized in that $R^6$ and $R^7$ are independently from each other selected from hydrogen; halogen; OH; SH; $NH_2$; a $C_{1-4}$-alkyl radical, which is linear or branched, and optionally at least mono-substituted by F, Cl, Br, I, SH or OH; and O—R with R being a $C_{1-4}$-alkyl radical, which is linear or branched, and optionally at least mono-substituted by F, Cl, Br, I, SH or OH.

7. Compound, or a salt thereof, according to claim 1, characterized in that $R^8$ is selected from hydrogen and a $C_{1-4}$-alkyl radical, which is linear or branched, and optionally at least mono-substituted by F, Cl, Br, I, SH or OH.

8. Compound, or a salt thereof, according to claim 1, selected from
1-[5-(1,3,5-Trimethyl-1H-pyrazol-4-yl)-1,2,3,4-tetrahydro-naphthalen-2-yl]-piperazine;
1-Methyl-4-[5-(1,3,5-trimethyl-1H-pyrazol-4-yl)-1,2,3,4-tetrahydro-naphthalen-2-yl]-piperazine;
1,3,5-Trimethyl-4-(6-pyrrolidin-1-yl-5,6,7,8-tetrahydro-naphthalen-1-yl)-1H-pyrazole;
1-[5-(1,3,5-Trimethyl-1H-pyrazol-4-yl)-1,2,3,4-tetrahydro-naphthalen-2-yl]-piperidine;
Dipropyl-[5-(1,3,5-trimethyl-1H-pyrazol-4-yl)-1,2,3,4-tetrahydro-naphthalen-2-yl]-amine;
Methyl-propyl-[5-(1,3,5-trimethyl-1H-pyrazol-4-yl)-1,2,3,4-tetrahydro-naphthalen-2-yl]-amine;
Diethyl-[5-(1,3,5-trimethyl-1H-pyrazol-4-yl)-1,2,3,4-tetrahydro-naphthalen-2-yl]-amine;
Ethyl-methyl-[5-(1,3,5-trimethyl-1H-pyrazol-4-yl)-1,2,3,4-tetrahydro-naphthalen-2-yl]-amine;
Dimethyl-[5-(1-methyl-1H-pyrazol-4-yl)-1,2,3,4-tetrahydro-naphthalen-2-yl]-amine;
[5-(3,5-Dimethyl-isoxazol-4-yl)-1,2,3,4-tetrahydro-naphthalen-2-yl]-dimethyl-amine;
(5-Furan-3-yl-1,2,3,4-tetrahydro-naphthalen-2-yl)-dimethyl-amine;
Dimethyl-(5-thiophen-3-yl-1,2,3,4-tetrahydro-naphthalen-2-yl)-amine;
(2S)-Isopropyl-methyl-[5-(1,3,5-trimethyl-1H-pyrazol-4-yl)-1,2,3,4-tetrahydro-naphthalen-2-yl]-amine;
(2S)-Isopropyl-propyl-[5-(1,3,5-trimethyl-1H-pyrazol-4-yl)-1,2,3,4-tetrahydro-naphthalen-2-yl]-amine;
(2S)-Ethyl-isopropyl-[5-(1,3,5-trimethyl-1H-pyrazol-4-yl)-1,2,3,4-tetrahydro-naphthalen-2-yl]-amine; and
4-[5-(1,3,5-Trimethyl-1H-pyrazol-4-yl)-1,2,3,4-tetrahydro-naphthalen-2-yl]-morpholine.

9. Compound, or a salt thereof, according to claim 1, selected from
[5-(3,5-Dimethyl-1H-pyrazol-4-yl)-1,2,3,4-tetrahydro-naphthalen-2-yl]-dimethyl-amine,
Dimethyl-[5-(1-methyl-1H-pyrazol-4-yl)-1,2,3,4-tetrahydro-naphthalen-2-yl]-amine,
(rac)-Dimethyl-[5-(1,3,5-trimethyl-1H-pyrazol-4-yl)-1,2,3,4-tetrahydro-naphthalen-2-yl]-amine; and
(2R)-Dimethyl-[5-(1,3,5-trimethyl-1H-pyrazol-4-yl)-1,2,3,4-tetrahydro-naphthalen-2-yl]-amine.

10. Process for the preparation of a compound, or a salt thereof, according to claim 1, characterized in that a compound of general formula III or IIIa,

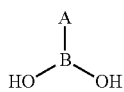

(III)

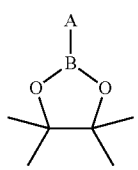

(IIIa)

wherein A has the meaning according to claim 3, is reacted with a compound according to general formula XII

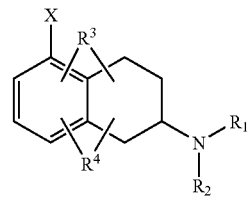

(XII)

wherein $R^1$, $R^2$, $R^3$ and $R^4$ have the meaning according to claim 3, and X represents halogen, OH, OMe or O-triflate group, in a suitable reaction medium, in the presence of a palladium catalyst, a suitable ligand and at least one base.

11. A composition comprising at least one compound, or a salt thereof, according to claim 1 and one or more pharmaceutically acceptable excipients.

12. A method for the or treatment of a 5-HT$_7$ mediated disease or condition wherein the disease is pain, which method comprises administering to a subject in need a therapeutically effective amount of at least one compound, or salt thereof, according to claim 1, and optionally one or more pharmaceutically acceptable excipients.

13. Process for the production of dimethyl-[5-(1,3,5-trimethyl-1H-pyrazol-4-yl)-1,2,3,4-tetrahydro-naphthalen-2-yl]-amine in which a compound according to formula XXIV

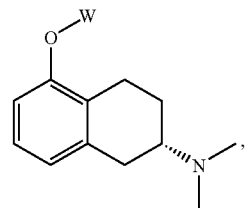

in which W is a leaving group, is reacted with a compound of Formula XXV

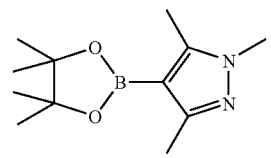

in the presence of a catalyst.

14. Compound, or a salt thereof, according to claim 3, characterized in that $R^1$ and $R^2$ are independently from each other CH$_3$, C$_2$H$_5$ or C$_3$H$_7$.

15. Compound, or a salt thereof, according to claim 4, characterized in that $R^1$ and $R^2$ together with their connecting nitrogen form an optionally at least mono-substituted heterocyclic ring system of 5 or 6 ring members.

16. Compound, or a salt thereof, according to claim 15, characterized in that $R^1$ and $R^2$ together with their connecting nitrogen are form a heterocyclic ring system selected from

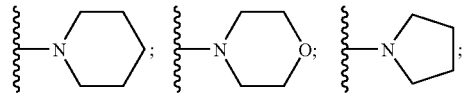

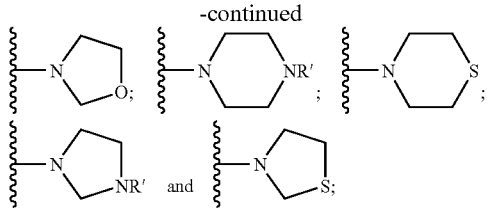

wherein R' is selected from hydrogen or a linear or branched $C_{1-4}$-alkyl radical.

17. Compound, or a salt thereof, according to claim 5, characterized in that $R^3$ and $R^4$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$.

18. Compound, or a salt thereof, according to claim 17, characterized in that $R^3$ and $R^4$ are H.

19. Compound, or a salt thereof, according to claim 6, characterized in that $R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$.

20. Compound, or a salt thereof, according to claim 19, characterized in that $R^6$ and $R^7$ are independently from each other selected from H, and $CH_3$.

21. Compound, or a salt thereof, according to claim 7, characterized in that $R^8$ is selected from H, $CH_3$, $C_2H_5$, $C_3H_7$, and $C_4H_9$.

22. Compound, or a salt thereof, according to claim 21, characterized in that $R^8$ is selected from H and $CH_3$.

23. Process according to claim 10 wherein X is bromine.

24. A method according to claim 12 wherein the pain is visceral pain, chronic pain, cancer pain, migraine, acute pain or neuropathic pain.

25. A method according to claim 12 wherein the pain is neuropathic pain, allodynia or hyperalgesia.

26. Process according to claim 13 wherein the leaving group is Tf and the catalyst is a palladium catalyst.

* * * * *

UNITED STATES PATENT AND TRADEMARK OFFICE
CERTIFICATE OF CORRECTION

PATENT NO. : 8,236,845 B2  Page 1 of 1
APPLICATION NO. : 12/593464
DATED : August 7, 2012
INVENTOR(S) : Garcia-Lopez et al.

It is certified that error appears in the above-identified patent and that said Letters Patent is hereby corrected as shown below:

Column 67, Line 66: Claim 10, Delete "claim 3" and insert -- claim 1 --

Column 68, Line 12: Claim 10, Delete "claim 3" and insert -- claim 1 --

Signed and Sealed this
Twenty-ninth Day of January, 2013

David J. Kappos
*Director of the United States Patent and Trademark Office*